(12) United States Patent
McDonald

(10) Patent No.: US 11,471,261 B2
(45) Date of Patent: Oct. 18, 2022

(54) VASCULAR GRAFT

(71) Applicant: VASCUTEK LIMITED, Glasgow (GB)

(72) Inventor: Gary McDonald, Glasgow (GB)

(73) Assignee: Vascutek Limited, Renfrewshire (GB)

( * ) Notice: Subject to any disclaimer, the term of this patent is extended or adjusted under 35 U.S.C. 154(b) by 125 days.

(21) Appl. No.: 16/336,806

(22) PCT Filed: Sep. 28, 2017

(86) PCT No.: PCT/GB2017/052916
§ 371 (c)(1),
(2) Date: Mar. 26, 2019

(87) PCT Pub. No.: WO2018/060716
PCT Pub. Date: Apr. 5, 2018

(65) Prior Publication Data
US 2019/0223996 A1 Jul. 25, 2019

(30) Foreign Application Priority Data

Sep. 30, 2016 (GB) .................................. 1616722

(51) Int. Cl.
*A61F 2/07* (2013.01)
*A61F 2/954* (2013.01)
(Continued)

(52) U.S. Cl.
CPC .................. *A61F 2/07* (2013.01); *A61F 2/06* (2013.01); *A61F 2/954* (2013.01); *A61F 2/97* (2013.01);
(Continued)

(58) Field of Classification Search
CPC .... A61F 2/07; A61F 2/06; A61F 2/954; A61F 2/97; A61F 2002/075; A61F 2002/9528;
(Continued)

(56) References Cited

U.S. PATENT DOCUMENTS

| 4,580,568 A | 4/1986 | Gianturco |
| 5,578,072 A | 11/1996 | Barone et al. |

(Continued)

FOREIGN PATENT DOCUMENTS

| AU | 2010254599 B1 | 2/2011 |
| EP | 0880979 A1 | 12/1998 |

(Continued)

OTHER PUBLICATIONS

International Search Report and Written Opinion issued in PCT Application No. PCT/GB2017/052916, dated Feb. 12, 2018, 20 pages.

(Continued)

*Primary Examiner* — Kelly J Bekker
*Assistant Examiner* — Andrew P. Restaino
(74) *Attorney, Agent, or Firm* — Foley Hoag LLP

(57) ABSTRACT

An endoprosthetic device comprises a tubular main body having a length including proximal and distal portions, the tubular main body having a flexible portion between the proximal and distal portions, and at least one adjustable length docking branch extending laterally from the tubular main body, and having sections bearing a tab or loop graspable by a user, and optionally further having at least one auxiliary branch, and at least one access branch, for assembly with at least one tubular branch body having a laterally extending access branch, using a delivery system including a delivery shaft, and a retrieval capsule and corresponding press-fit retrieval pin and retrieval wire, wherein the delivery shaft is provided with a pivotal slotted housing serving as a user handle for the delivery shaft.

14 Claims, 27 Drawing Sheets

(51) Int. Cl.
   *A61F 2/97*    (2013.01)
   *A61F 2/06*    (2013.01)
   *A61F 2/95*    (2013.01)

(52) U.S. Cl.
   CPC ... *A61F 2002/061* (2013.01); *A61F 2002/075* (2013.01); *A61F 2002/9528* (2013.01); *A61F 2250/006* (2013.01); *A61F 2250/0007* (2013.01); *A61F 2250/0069* (2013.01)

(58) Field of Classification Search
   CPC ........ A61F 2250/0069; A61F 2002/061; A61F 2250/0007; A61F 2250/006; A61F 2/844; A61F 2/856; A61F 2/95; A61F 2/962; A61F 2002/826; A61F 2002/9505; A61F 2250/0064; A61F 2250/0062; A61F 2/9522
   See application file for complete search history.

(56) References Cited

U.S. PATENT DOCUMENTS

| | | | |
|---|---|---|---|
| 6,036,723 | A | 3/2000 | Anidjar et al. |
| 6,773,457 | B2 | 8/2004 | Ivancev et al. |
| 7,901,446 | B2 | 3/2011 | Fitzpatrick et al. |
| 8,088,155 | B1 | 1/2012 | Lauterjung |
| 8,088,159 | B2 | 1/2012 | Lauterjung |
| 8,092,511 | B2 | 1/2012 | Chuter |
| 8,486,129 | B2 | 7/2013 | Lautherjung |
| 8,652,195 | B2 | 2/2014 | Tani |
| 8,740,971 | B2 | 6/2014 | Iannelli |
| 8,968,389 | B2 | 3/2015 | Greenberg et al. |
| 9,398,964 | B2 | 7/2016 | McGee et al. |
| 9,510,936 | B2 | 12/2016 | McDonald et al. |
| 9,622,894 | B2 | 4/2017 | McGee |
| 9,993,329 | B2 | 6/2018 | McDonald et al. |
| 10,137,021 | B2 | 11/2018 | McDonald et al. |
| 10,219,890 | B2 | 3/2019 | Madjarov et al. |
| 11,026,823 | B2 | 6/2021 | McDonald et al. |
| 2003/0024527 | A1 | 2/2003 | Ginn |
| 2003/0120263 | A1 | 6/2003 | Ouriel et al. |
| 2003/0130720 | A1 | 7/2003 | DePalma et al. |
| 2004/0117003 | A1 | 6/2004 | Ouriel et al. |
| 2004/0167618 | A1 | 8/2004 | Shaolian |
| 2005/0060029 | A1 | 3/2005 | Le et al. |
| 2005/0075725 | A1 | 4/2005 | Rowe |
| 2005/0137681 | A1 | 6/2005 | Shoemaker et al. |
| 2005/0230956 | A1 | 10/2005 | Igeta |
| 2007/0010873 | A1 | 1/2007 | Neri |
| 2007/0106368 | A1 | 5/2007 | Vonderwalde |
| 2007/0112422 | A1 | 5/2007 | Dehdashtian |
| 2007/0135904 | A1 | 6/2007 | Eidenschink |
| 2007/0168013 | A1 | 7/2007 | Douglas |
| 2008/0082159 | A1 | 4/2008 | Tseng et al. |
| 2008/0147171 | A1 | 6/2008 | Ashton et al. |
| 2009/0264991 | A1 | 10/2009 | Paul, Jr. et al. |
| 2010/0234937 | A1 | 9/2010 | Wang et al. |
| 2011/0190862 | A1* | 8/2011 | Bashiri ............ A61F 2/95 623/1.11 |
| 2011/0230956 | A1 | 9/2011 | White |
| 2012/0059448 | A1 | 3/2012 | Parker et al. |
| 2012/0136431 | A1* | 5/2012 | Chen ............ A61F 2/07 623/1.35 |
| 2012/0158121 | A1 | 6/2012 | Ivancev et al. |
| 2012/0172887 | A1 | 7/2012 | Hatfield |
| 2012/0277849 | A1 | 11/2012 | Tani et al. |
| 2013/0131775 | A1 | 5/2013 | Hadley et al. |
| 2013/0166015 | A1 | 6/2013 | Roeder |
| 2013/0218138 | A1 | 8/2013 | Fargahi |
| 2013/0289713 | A1 | 10/2013 | Pearson et al. |
| 2014/0005586 | A1 | 1/2014 | Feinstein |
| 2014/0194970 | A1 | 7/2014 | Chobotov |
| 2014/0200648 | A1 | 7/2014 | Newell et al. |
| 2014/0257452 | A1 | 9/2014 | Slazas et al. |
| 2014/0277332 | A1 | 9/2014 | Slazas et al. |
| 2014/0277345 | A1 | 9/2014 | Havel et al. |
| 2014/0277359 | A1 | 9/2014 | Slazas et al. |
| 2015/0081004 | A1 | 3/2015 | Takahashi et al. |
| 2015/0105819 | A1* | 4/2015 | Becking ............ A61M 25/0012 606/200 |
| 2015/0265444 | A1 | 9/2015 | Kitaoka |
| 2019/0192273 | A1 | 6/2019 | Debus et al. |
| 2019/0223996 | A1 | 7/2019 | McDonald |
| 2020/0038169 | A1 | 2/2020 | Nelis |
| 2020/0038184 | A1 | 2/2020 | McLean |
| 2020/0038211 | A1 | 2/2020 | Kolbel et al. |
| 2020/0214821 | A1 | 7/2020 | McDonald |
| 2021/0212846 | A1 | 7/2021 | Shahriari |
| 2021/0228330 | A1 | 7/2021 | Kelly |
| 2021/0236257 | A1 | 8/2021 | Walzman |
| 2021/0307641 | A1 | 10/2021 | Rumbles et al. |

FOREIGN PATENT DOCUMENTS

| | | | |
|---|---|---|---|
| EP | 1847236 | A2 | 10/2007 |
| EP | 3248572 | A1 | 11/2017 |
| JP | H07308330 | A | 11/1995 |
| WO | WO-2004/064686 | A1 | 8/2004 |
| WO | WO-2008/057569 | A1 | 5/2008 |
| WO | WO-2008088835 | | 7/2008 |
| WO | WO-2008/112270 | A1 | 9/2008 |
| WO | 2009009376 | A2 | 1/2009 |
| WO | WO-2009/082718 | A1 | 7/2009 |
| WO | WO-2009/153768 | A1 | 12/2009 |
| WO | WO-2010/053563 | A1 | 5/2010 |
| WO | 20140163957 | A1 | 10/2014 |
| WO | WO-2016075615 | A3 | 6/2016 |
| WO | WO-2017/136733 | A1 | 8/2017 |
| WO | 20170203056 | A1 | 11/2017 |
| WO | WO-2018/060716 | A1 | 4/2018 |

OTHER PUBLICATIONS

Search Report dated Aug. 8, 2017 issued by the Intellectual Property Office of the United Kingdom for Application No. GB1616722.3, 5 pages.
Search Report dated Apr. 13, 2018 issued by the Intellectual Property Office of the United Kingdom for Application No. GB1616722.3, 2 pages.
Japanese Examination Report for JP Application No. 2019-516423 dated Jul. 27, 2021, 8 pages.
United Kingdom Examination Report for GB Application No. 1616722.3 dated Jun. 10, 2021, 2 pages.
Shrestha et al., "Total aortic arch replacement with a novel 4-branched frozen elephant trunk prosthesis: Single-center results of the first 100 patients," Journal of Thoracic and Cardiovascular Surgery, 152(1): 148-159 (2016).

* cited by examiner

VASCULAR GRAFT

CROSS REFERENCE TO RELATED APPLICATIONS

This application is a U.S. National Phase filing under 35 U.S.C. § 371 of International Application PCT/GB2017/052916, filed Sep. 28, 2017, and published as WO 2018/060716 on Apr. 5, 2018. PCT/GB2017/052916 claims priority from United Kingdom application number 1616722.3, filed Sep. 30, 2016. The entire contents of each of these prior applications are hereby incorporated herein by reference.

TECHNICAL FIELD

This disclosure relates to surgical procedures and provides a prosthetic device for use as a hybrid endograft in a patient requiring surgery, particularly an intervention to treat a vascular pathology.

BACKGROUND OF THE INVENTION

Parts of the vascular system may develop degenerative defects over time, and one such defect is an aneurysm. An aneurysm is an abnormal bulge in the wall of a blood vessel leading to a localised weakening of the blood vessel wall with an increased potential for leakage, rupture and internal bleeding. The aneurysm may cause significant dilation of the natural (native) lumen of the blood vessel compromising natural blood flow. The present disclosure relates to an endograft suitable for insertion into the aneurysm sac in the defective blood vessel to restore the vessel lumen dimensions to those of the natural blood vessel before the aneurysm developed and thereby occlude the aneurysm sac. The disclosed device is suitable for endoluminal treatment of the aortic arch including the ascending and descending aorta and branch arteries; left subclavian artery, left common carotid artery, brachiocephalic artery, right common carotid artery.

Conventional methods for treatment of weakened portions of the vasculature include surgical replacement of the affected portion of the aorta, or a more conservative, minimally invasive endovascular repair.

In surgical intervention, the affected part of the blood vessel can be excised and replaced with a prosthetic graft. This invasive approach is normally performed under general anaesthesia with cardiopulmonary by-pass, so that the patient's thorax can be opened and the prosthesis sutured in place of the aneurysmal vessel. Consequently, the method requires the time of a skilled surgeon and prolonged recovery periods for the patient in hospital. Prosthetic grafts normally used for such replacement are typically made from polyester fabric, which may be woven or knitted, and may be sealed with a sealant, for example gelatine or collagen.

The endovascular repair techniques use endoprosthetic devices which are placed within the patient using bespoke delivery systems designed to deliver the endoprosthetic device in a compact "packaged" form for intraluminal delivery, and including removable restraining means, allowing the endoprosthetic device to be delivered, positioned, and finally selectively deployed. When the endoprosthetic device is deployed, the delivery system is removed, allowing the surgical procedure to be completed.

Hybrid procedures combine a conventional or modified surgical procedure with an endovascular intervention procedure and are feasible in selected high surgical risk patients. For example use of hybrid procedures provides an alternative to open repair in high risk surgical patients with complex aortic pathology. A vascular endoprosthesis apt to exclude an aneurysmal portion of the aorta is disclosed in U.S. Pat. No. 8,740,971 B2 the content of which is incorporated herein by reference.

Whereas there is a continuing need to improve surgical procedures and endoprosthetic devices suitable for addressing patient needs, endoprosthetic devices and methods disclosed herein offer the ability to create an arterial anastomosis with reduced risk of detrimental tension whilst having sufficient scope for manoeuvre during the procedure.

Additionally, the endoprosthetic devices and methods disclosed herein permit blood flow sooner than before, with the ability to expel air from an endoprosthetic device by displacement through a valve feature of blood flow into the endoprosthetic device.

SUMMARY OF THE INVENTION

Using the hybrid endoprosthetic devices disclosed herein in a known procedure or in a procedure modified as disclosed herein permits rapid perfusion of aortic arch branch arteries by anti-grade blood flow whereby subsequent steps required to complete a procedure can be conducted thereafter at an acceptable pace with a foreseeable reduction in risk of ischemia or related problems normally associated with the known procedures. Therefore, the usual time pressure to complete the procedure is somewhat lessened. Significantly, the procedures described in this disclosure are designed to be carried out whilst the patient's heart remains beating, i.e. the patient is not supported on a "heart-lung" machine and so the procedure is classed as an "off-pump" procedure which offers numerous advantages. Nevertheless it is not exclusively restricted to "off-pump" procedures and can be usefully employed due to time savings in "on-pump" procedures where the patient is supported on a "heart-lung" machine.

The term "aortic arch branch arteries" is generally understood to encompass the left subclavian artery, left common carotid artery, right common carotid artery and brachiocephalic artery. Connection of these arteries to an endoprosthetic device is provided for in the following disclosure using newly conceived devices and modifications thereof to be more particularly described herein.

Broadly this disclosure relates to an endoprosthetic device useful in a hybrid surgical procedure, that serves as a substitute for a deteriorated or injured part of a natural vessel, and is configured for flow connection with adjacent natural vessels normally communicating with the deteriorated or injured part of a natural vessel. In particular embodiments, the endoprosthetic device may substitute part of the aortic arch region of the vasculature, and has lateral branches for connection with aortic arch branch vessels. According to aspects to be more particularly described herein below, a device enabling early perfusion in a procedure is disclosed.

According to an aspect, an endoprosthetic device comprises a tubular main body having a length including proximal and distal portions, the tubular main body having a flexible portion between the proximal and distal portions, and is provided with at least one adjustable length docking branch extending laterally from the tubular main body. In embodiments, the endoprosthetic device has at least one access branch. Such an access branch may be positioned on the tubular main body and configured to permit access to a docking branch. Such an access branch may be useful for delivery of a modular component through the docking branch.

In embodiments at least one of the proximal and distal portions of the tubular main body includes a stent.

In embodiments the proximal and distal portions of the tubular main body each include a stent.

Provision of an adjustable length docking branch addresses the frequent problem of anatomical variance in the vasculature of patients.

In embodiments the adjustable length docking branch comprises a crimped fabric sleeve over at least a portion of its adjustable length, enabling the docking branch to be stretched lengthwise, and when required curved in a desired direction.

In embodiments, the crimped fabric comprises expanded polytetrafluoroethylene (ePTFE) or polyester.

The term "crimped" as used in the present disclosure relates to a fabric profile having a circumferential corrugation or spiral profile which when viewed from a side has a generally zig-zag outline or sinusoidal profile wherein the exterior surface undulates from a maximum dimension to a minimum dimension repeatedly over a substantial length of the docking branch. Such a crimped profile permits additional length for the docking branch to be obtained by applying a longitudinal stretch. Alternatively a reduced length can be obtained by applying a longitudinal compression. Additionally the crimp surface also accommodates bending of the docking branch to accommodate re-direction of the docking branch from straight profile to a curved profile which may be required for connection with a native vessel and to account for vascular variance in patients.

In embodiments, the adjustable length docking branch has a length comprising a series of sections, each section having a tab which may be gripped to facilitate trimming of the length of the docking branch.

In embodiments each section has a holding loop instead of a tab which improves the ability to grasp and hold the docking branch for trimming under the slippery conditions of the surgical procedure due to the presence of body fluids.

The tab or loop can be made of a biocompatible material such as a polyester fabric, polyethylene or ePTFE.

In embodiments, the endoprosthetic device is provided with at least one auxiliary branch extending from the tubular main body. The auxiliary branch may be used for a variety of tasks, for example perfusion of the endoprosthetic device, insertion and removal of a surgical tool, or for delivery or removal of components of another device or components of a delivery system.

In embodiments, the, or each auxiliary branch may include an integrated valve to enable at least one of air removal, flushing and perfusion.

According to another aspect a vascular graft is provided as a modular assembly comprising at least one additional component for use with the endoprosthetic device disclosed herein wherein the additional component comprises a tubular branch body having a length including proximal and distal stented portions, the tubular branch body having a flexible portion between the proximal and distal stented portions, and is configured to connect with a docking branch of the endoprosthetic device to form a vascular graft modular assembly.

The tubular branch body may have a laterally extending access branch for a delivery system component or device.

A plurality of such modular components may be provided for attachment respectively to multiple docking branches of the tubular main body.

The provision of a plurality of modular components addresses the problems associated with use of pre-formed one piece multi-branch endoprosthetic devices. Therefore a more flexible and versatile endoprosthetic device is available to the surgeon.

The endoprosthetic device may comprise a modular assembly of a tubular main body and a plurality of tubular branch bodies selected from a kit of modular components comprising a tubular main body, and a plurality of tubular branch bodies wherein the plurality of tubular branch bodies may include tubular branch bodies of the same or differing dimensions to anticipate anatomical variance. For example the tubular branch bodies may be of differing lengths. Optionally the tubular branch bodies may have a tapered length portion.

Whereas endovascular procedures typically involve delivery of endoprosthetic devices in a compact form for expansion within a natural vessel lumen, by use of balloon expansion or by use of compressed resilient stents, the embodiments of the present modular assembly usefully employ multiple stented sections within the proximal and distal portions of the tubular main body and of the or each tubular branch body to facilitate rapid circumferential anastomoses. This feature, in the anticipated procedure in most cases, obviates the need to fully suture the junction of the parts connected by the stented portion.

The endoprosthetic device offers procedural advantages as a modular assembly of the tubular main body and plurality of tubular branch bodies by virtue of enabling a staged (sequential) deployment following insertion through a natural vessel side wall. The compact nature of the modular parts offers a low size profile during the staged deployment procedure. This facilitates the provision of substantially continuous blood flow and provides an ability to reduce ischemia time period.

Furthermore, the staged (sequential) insertion and deployment that is made possible by use of a modular assembly of the tubular main body and plurality of tubular branch bodies also allows the surgical procedure to proceed without the need for a full thoracotomy, avoiding generally the need to place the patient on a heart lung machine. Thereby, the normal risks of induced hypothermia and cardiac arrest associated with a major surgical opening of the chest cavity are also mitigated.

The disclosed modular assembly provides a sealed system that can minimise blood loss and maintain blood perfusion during the surgical procedure.

The modular assembly may mimic the structure of a natural main vessel and associated branch vessel(s).

According to another aspect a delivery system for the vascular graft modular assembly including the endoprosthetic device comprises a sheath for confining a tubular branch body in a compact form for delivery through a lumen, a retrieval capsule and a press-fit retrieval pin configured to fit within the retrieval capsule, and a retrieval wire having a proximal end and a distal end, wherein one of the retrieval capsule and a press-fit retrieval pin is attached to the sheath and the other is attached to the distal end of the retrieval wire, the proximal end of the retrieval wire being available to a user of the system.

In an embodiment, the press-fit retrieval pin may be attached to the sheath whilst the retrieval capsule is attached to the retrieval wire.

In an embodiment, the press-fit retrieval pin has a head portion of a shape enabling it to be captured within a corresponding recess in the retrieval capsule. The shape may be a ball, bullet or arrowhead and the head portion may be made from a resilient material allowing a degree of compression of the head portion during press-fitting into the retrieval capsule and elastic expansion of the head portion when the head portion is located in the corresponding recess in the retrieval capsule.

The retrieval capsule may be part of a retrieval capsule assembly having an external wall configured to form a sealing close fit within a docking branch so as to serve as a movable hemostat within the docking branch so as to minimise blood loss prior to connection of the tubular branch body to the docking branch by deployment of a stented portion of the tubular branch body therein.

In use of such an embodiment for an endoprosthetic device having a tubular main body with at least one docking branch extending laterally from the tubular main body, a user presents a tubular branch body having stented portions in a compact form within a sheath, and having a press-fit retrieval pin attached to the sheath, in juxtaposition with a retrieval capsule with attached retrieval wire previously passed through the tubular main body via an access or auxiliary branch, the retrieval pin is press-fitted into the retrieval capsule, the tubular branch body is then insertable into a docking branch of the main body of the endoprosthetic device, and by pulling upon the retrieval wire, the tubular branch body is first positioned in the docking branch of the main body of the endoprosthetic device and thereafter the stented portions of the tubular branch body may be deployed by removal of the sheath via the access or auxiliary branch.

The manner of removal of the sheath is not limited, and for that purpose a pull strap, pull wire, or pull cord can be used to initiate removal. The sheath may be designed to facilitate removal by having tearable parts, for example a lengthwise axial tear line which can be torn by contact with a pull wire to part the sheath lengthwise. Alternatively, the delivery system may incorporate a slitting tool and the sheath may be designed to split (tear) in a predictable and controllable manner under application of appropriately applied force when in contact with the slitting tool.

The sheath may comprise a smooth polymeric material. A polymerised hydrofluorocarbon such as PTFE is suitable. Alternatively the sheath may be formed from polyethyleneterephthalate (PET). The selected material should be one which is biocompatible and may be readily passed through natural vessels or artificial lumens without sticking. The sheath may be surface treated, for example to impart or enhance hydrophilic properties by applying a hydrophilic coating.

Suitable polymeric flexible materials for the sheath may be selected from thermoplastic polymers, elastomers, and copolymers such as nylon, polyurethane, polyethylene (PE), polytetrafluoroethylene (PTFE), expanded polytetrafluoroethylene (ePTFE), fluorinated ethylene propylene, polyether block amides (PEBA), polyimide, polyether ether ketone, and polybutylene terephthalate.

The sheath may be of a multi-layered construction of flexible, polymeric materials, such as multi-layered extrusions, optionally reinforced as by use of braided layered assemblies or laminar structures incorporating bonding layers and reinforcements, or intermittent extruded composite extrusions and assemblies of variable durometer characteristics.

According to another aspect a valve and air venting capability is introduced into an auxiliary or access branch of the main tubular body by provision of at least a removable valve and an integral valve deliverable upon a delivery shaft.

The removable valve may comprise a C-clamp portion of a pivotal slotted housing mounted upon the delivery shaft, the C-clamp portion being configured to clamp over a fabric tubular body positioned upon the delivery shaft.

The valve and air venting capability may comprise a slotted housing configured around a delivery shaft upon which a device may be mounted and constrained in a compact form within a removable sheath, the slotted housing forming a removable C-shape clamp valve part about the delivery shaft and compact endoprosthetic device positioned upon the delivery shaft. The housing may be pivotally mounted upon the delivery shaft to allow the C-shape clamp valve part to be removed from gripping about the delivery shaft and endoprosthetic device during or after deployment of the endoprosthetic device by removal of the sheath. The pivotal mounting for the housing may be located and spaced distally on the delivery shaft with respect to the position of the C-shape valve part. The housing may also enclose an integral valve and vent positioned upon the delivery shaft, which integral valve and vent may be resident within the access branch of the device after removal of the delivery shaft, and removed subsequently in the procedure when the access branch is to be cut down and sutured closed, the integral valve and vent being removable with the cut off access branch fabric to be disposed of.

The housing may be configured to serve as a user handle for manipulation and control of the delivery system.

The handle may have an internal chamber within which an integral valve deliverable upon the delivery shaft can be positioned for delivery purposes.

BRIEF DESCRIPTION OF DRAWINGS

Further details of the disclosed endoprosthetic devices and methods of use thereof are disclosed in the following description referring to the accompanying illustrative drawings in which.

DETAILED DESCRIPTION OF THE INVENTION

Figure 1:
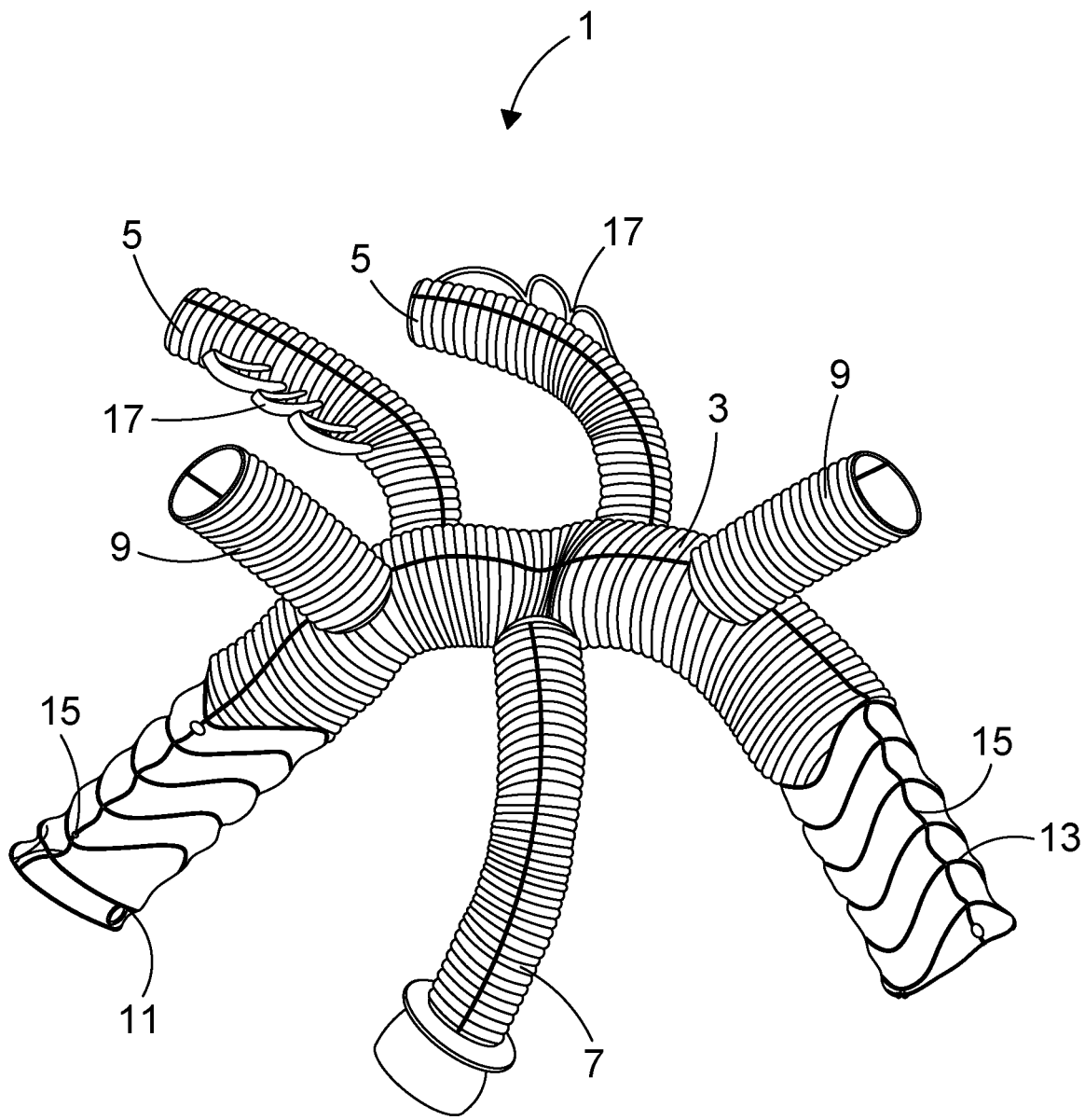
FIG. 1 shows a side view of a tubular prosthetic device having endovascular stented proximal and distal portions, docking branches, access branches and an auxiliary branch.

With reference to FIG. 1, there is shown an endoprosthetic device 1. The endoprosthetic device 1 comprises a tubular main body 3 having a length including proximal 11 and distal portions 13, the tubular main body having a flexible portion between the proximal 11 and distal portions 13, and is provided with at least one adjustable length docking branch 5 extending laterally from the tubular main body 3.

In embodiments, the endoprosthetic device 1 has at least one access branch 7. Such an access branch 7 may be positioned on the tubular main body 3 and configured to permit access to a docking branch 5. Such an access branch 7 may be useful for delivery of a modular component through the docking branch 5.

In embodiments at least one of the proximal 11 and distal portions 13 of the tubular main body includes a stent 15.

In embodiments the adjustable length docking branch 5 comprises a crimped fabric sleeve enabling the docking branch 5 to be stretched lengthwise, and when required curved in a desired direction.

In embodiments, the adjustable length docking branch 5 has a length comprising a series of sections, each section having a tab which may be gripped to facilitate trimming of the length of the docking branch 5. However, in the depicted example, each section has a holding loop 17 instead of a tab which improves the ability to grasp and hold the docking branch 5 for trimming under the slippery conditions of the surgical procedure due to the presence of body fluids. The tab or loop 17 can be made of a biocompatible material such as a polyester fabric.

In embodiments, the endoprosthetic device 1 is provided with at least one auxiliary branch 7 extending from the tubular main body 3. The auxiliary branch 7 may be used for a variety of tasks, for example perfusion of the endoprosthetic device 1, insertion and removal of a surgical tool, or for delivery or removal of components of another device or components of a delivery system.

In embodiments, the, or each auxiliary branch 7 may include an integrated valve to enable air removal and system flushing.

The device 1 is also provided with main body access branches 9 which extend from the main tubular body 3.

Figure 2:
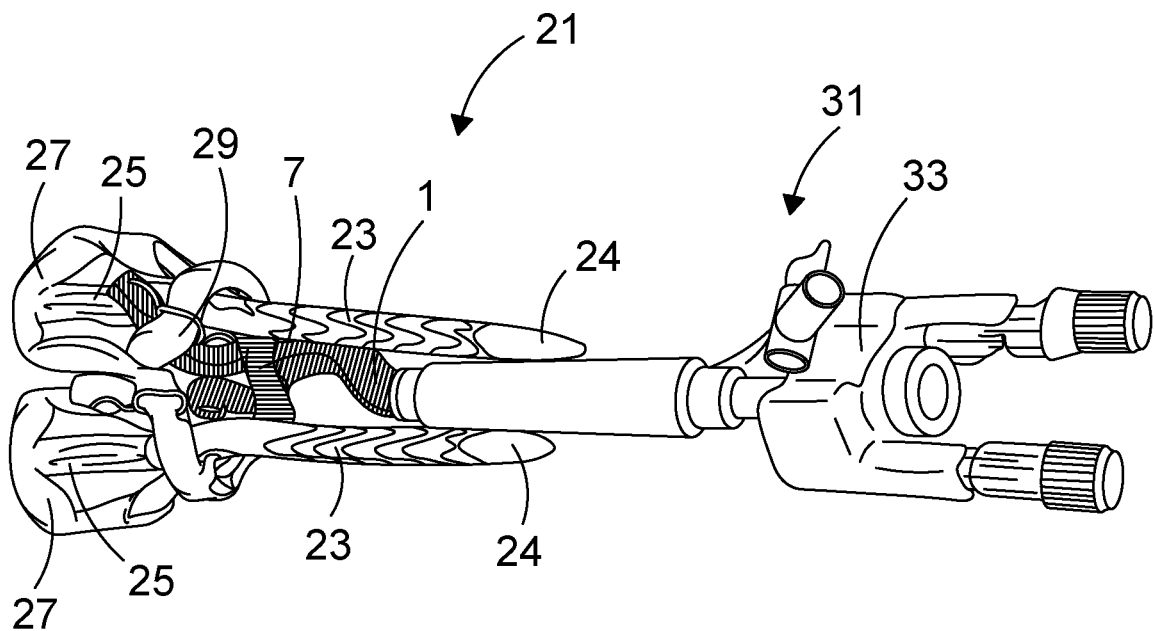
FIG. 2 shows a side view of a tubular prosthetic device compactly packed within a delivery system with an associated valved retrieval system for use with a modular component.

With reference to FIG. 2, there is shown an example delivery system 21 for the device 1. The system 21 includes main tubular body sheaths 23 for confining proximal 11 and distal portions 13 portions of the tubular main body 3 upon a delivery shaft. Each sheath 23 is attached to a capsule support holder 29, and is provided with a splitter 25 and a handle 27 for a surgeon to grip. Each delivery shaft has a tip 24 to facilitate insertion and passage thereof through a lumen.

The delivery system 21 also includes a modular component delivery system, which shall be described in more detail below. In FIG. 2, a first portion of the modular component delivery system 31 is depicted attached to the access branch 7, and comprises a branch valve 33.

Figure 3:
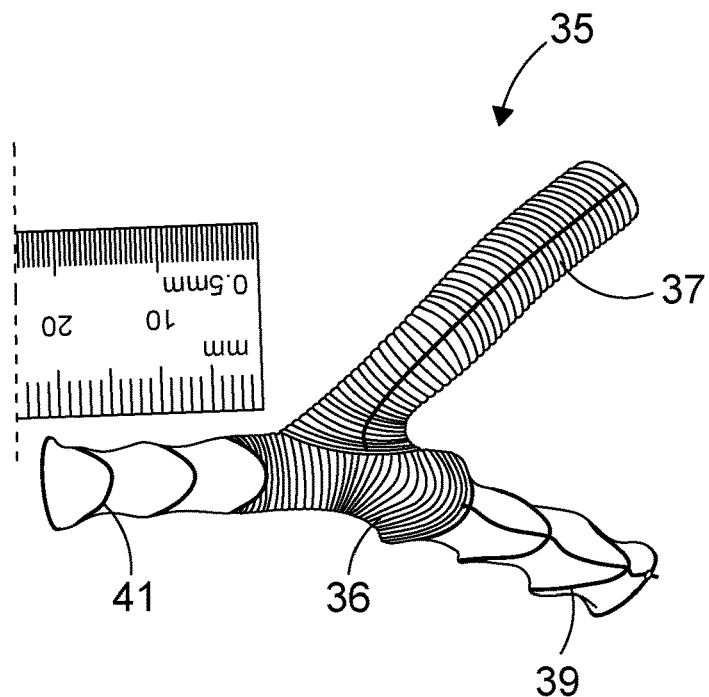
FIG. 3 shows a modular tubular branch device suitable for use with a tubular prosthetic device to form a modular assembly.

With reference to FIG. 3, there is shown a modular component 35 for use with the endoprosthetic device 1 disclosed herein. The component 35 comprises a tubular branch body 36 having a length including proximal and distal stented portions 39, 41. With reference to FIGS. 1 and 3, the tubular branch body 36 has a flexible portion between the proximal and distal stented portions 39, 41, and is configured to connect with a docking branch 5 of the endoprosthetic device 1 to form a modular assembly.

The tubular branch body 36 may have a laterally extending access branch 37 for a delivery system component or device. A plurality of such modular components 35 may be provided for attachment respectively to multiple docking branches 5 of the tubular main body 3.

The endoprosthetic device 1 may comprise a modular assembly of a tubular main body 3 and a plurality of tubular branch bodies selected from a kit of modular components comprising a tubular main body 3, and a plurality of tubular branch bodies wherein the plurality of tubular branch bodies may include tubular branch bodies of the same or differing dimensions to anticipate anatomical variance. For example the tubular branch bodies may be of differing lengths. Optionally the tubular branch bodies may be tapered.

Figure 4:
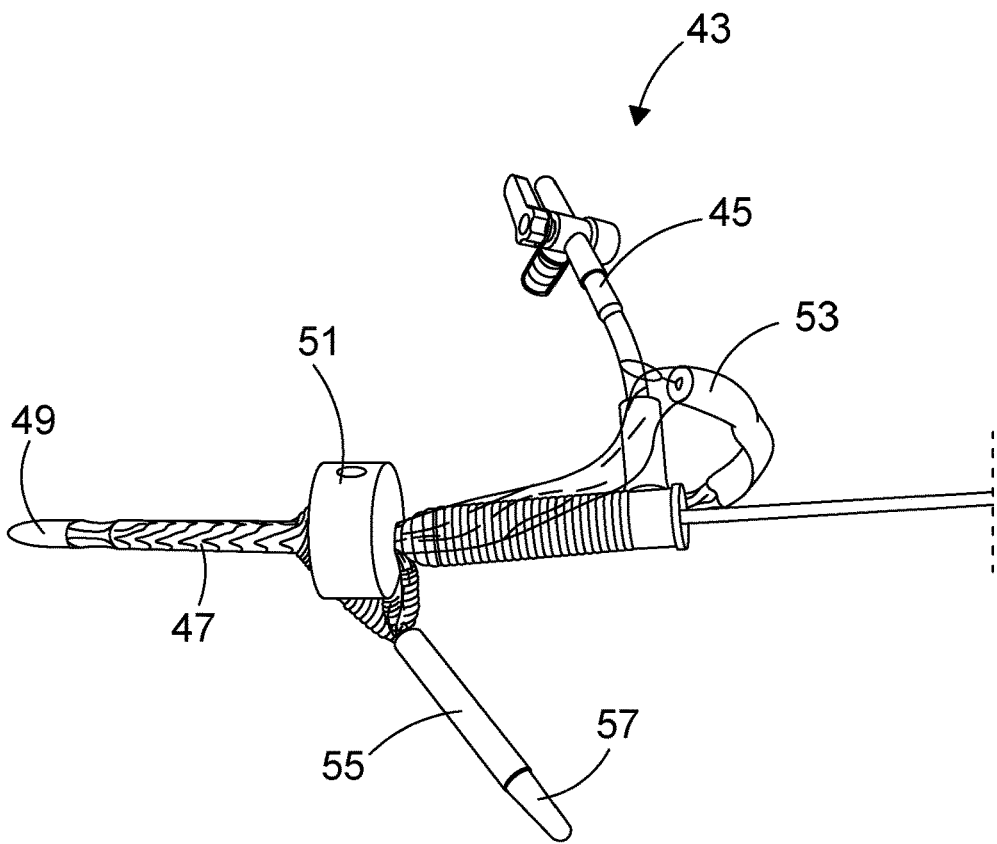
FIG. 4 shows a delivery system for introducing a modular tubular branch device compactly mounted within the delivery system.
Figure 5:
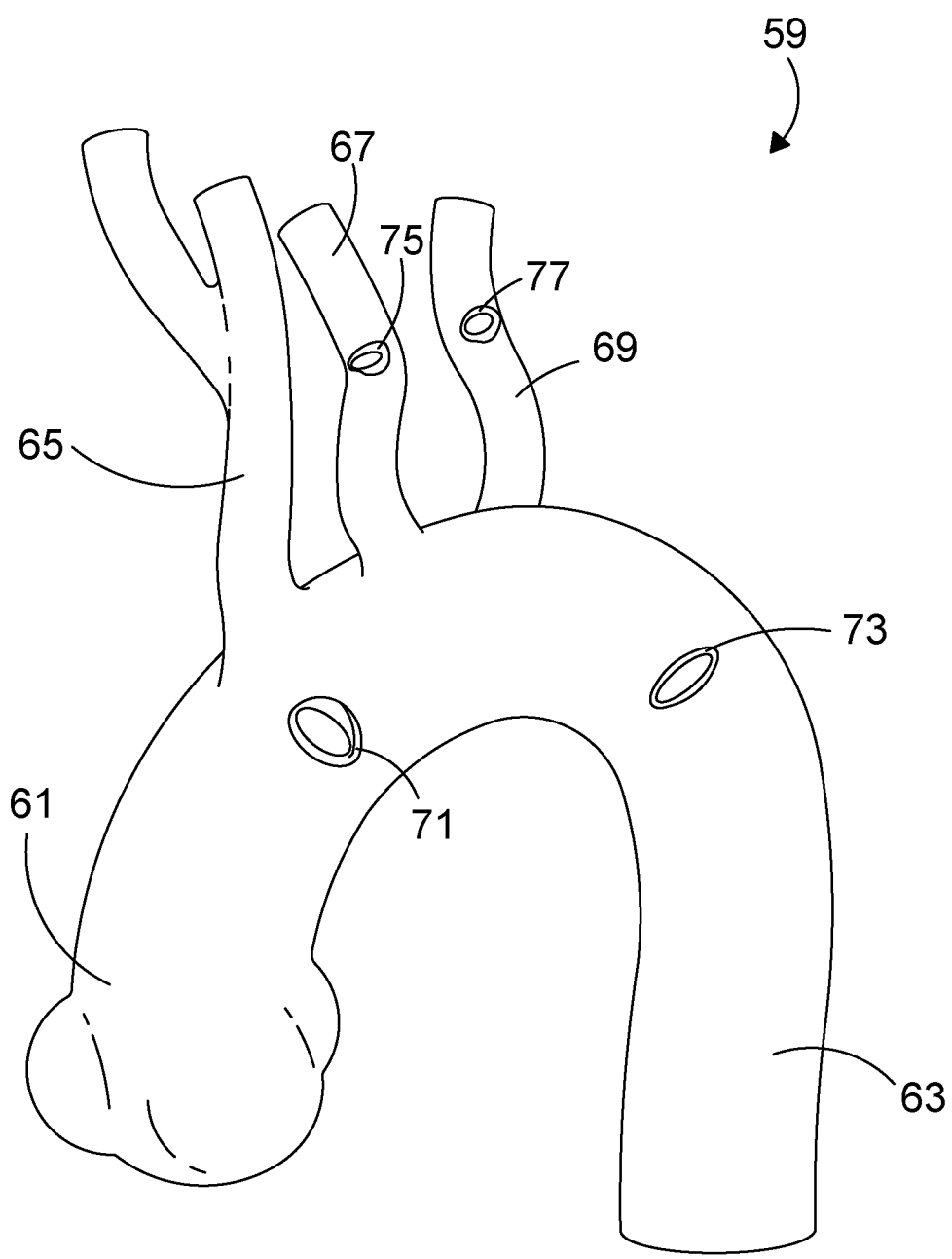
FIG. 5 illustrates a part of the vasculature (aortic arch and associated major vessels) with purse string incisions for endovascular insertion of a tubular prosthetic device having a main tubular body which is flexible and has endovascular end portions.
Figure 6:
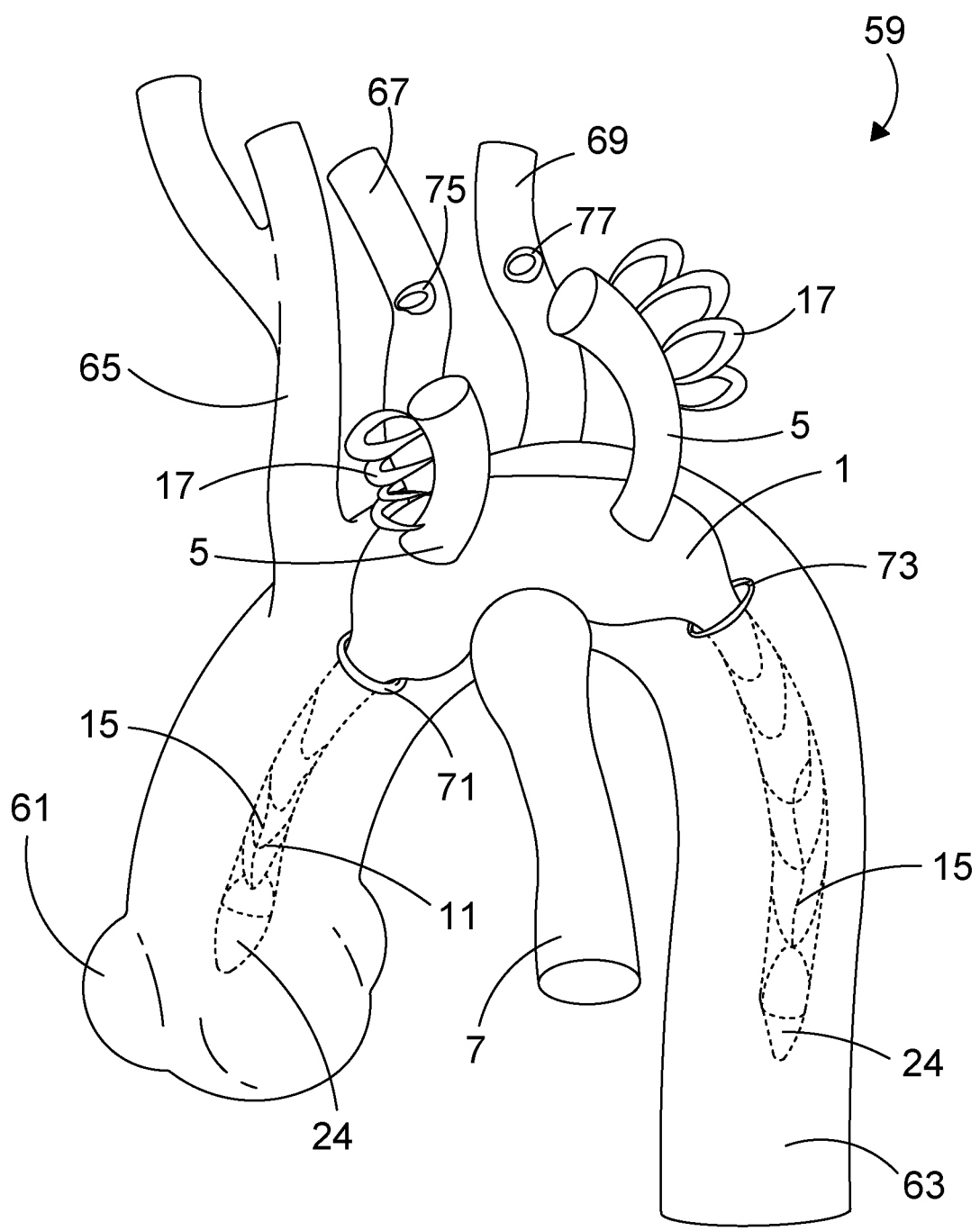
FIG. 6 illustrates a tubular prosthetic device having a main tubular body which is flexible and has compact sheathed endovascular stented end portions and adjustable length docking branches, where the sheathed endovascular end portions have been inserted into the purse string incisions.
Figure 7:
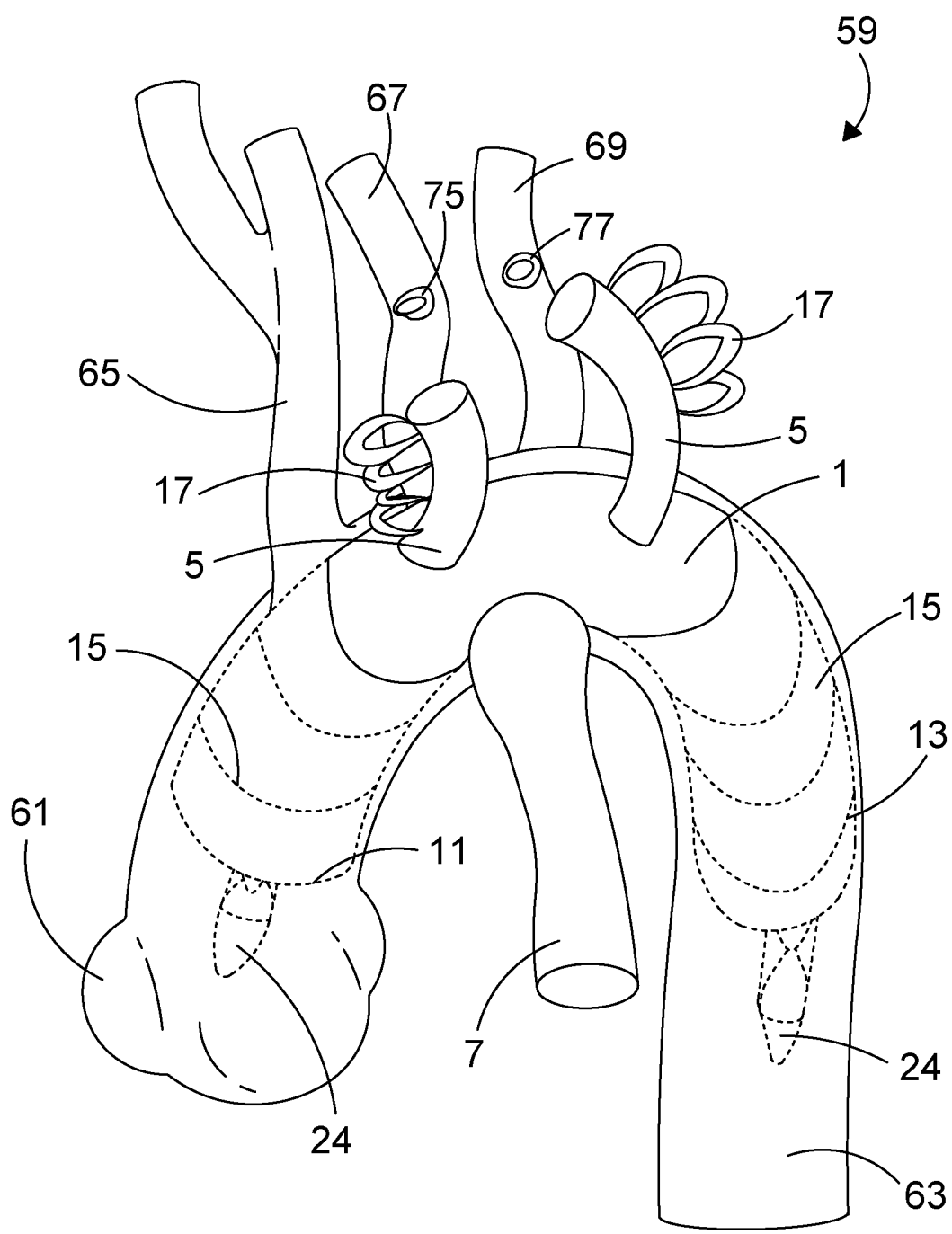
FIG. 7 illustrates the tubular prosthetic device of FIG. 6 wherein the endovascular stented end portions have been deployed by removal of respective sheaths.
Figure 8:
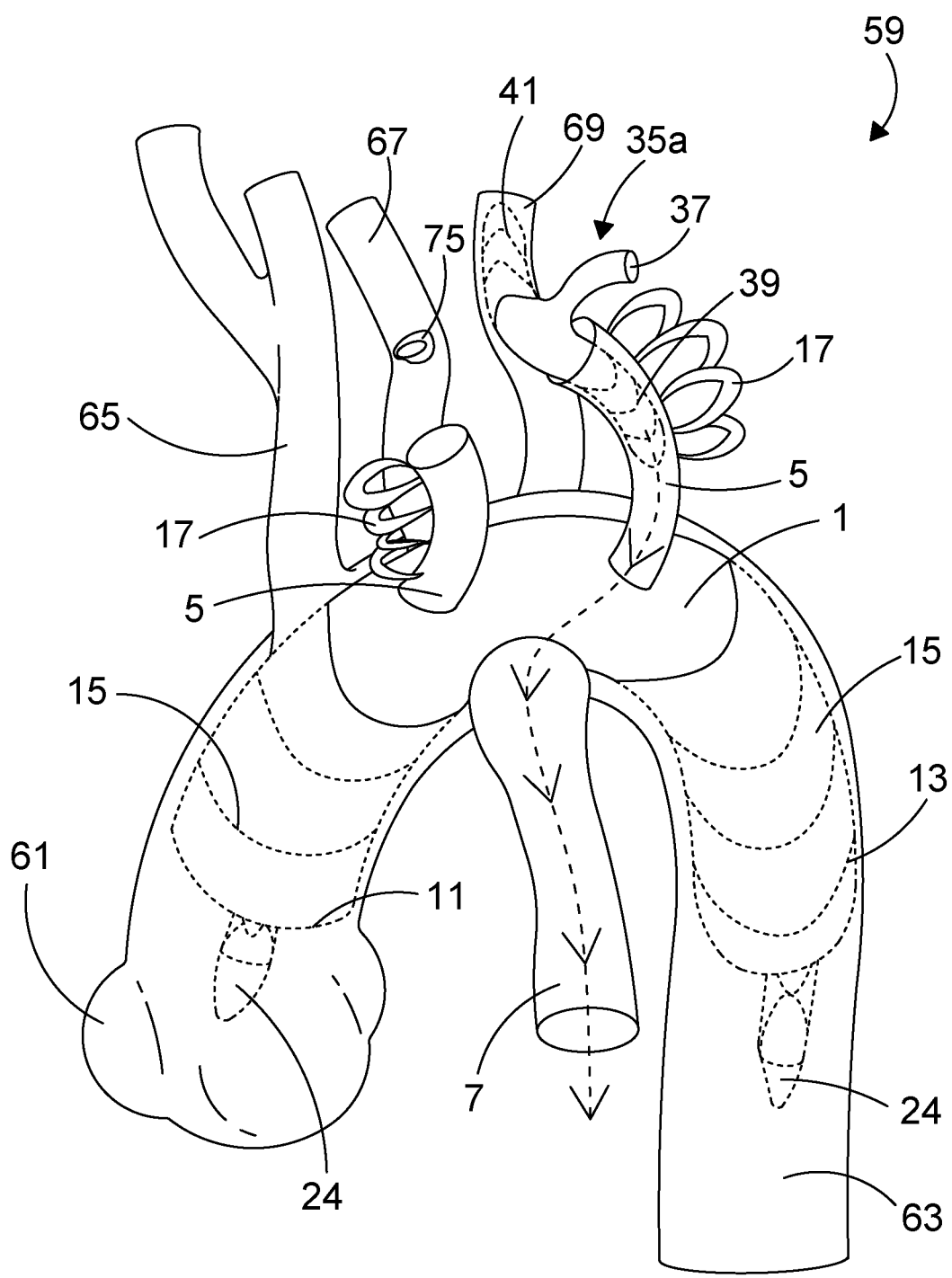
FIG. 8 illustrates the introduction of a tubular branch body into a docking branch of the tubular prosthetic device of FIGS. 6 and 7 to form a modular assembly.
Figure 9:
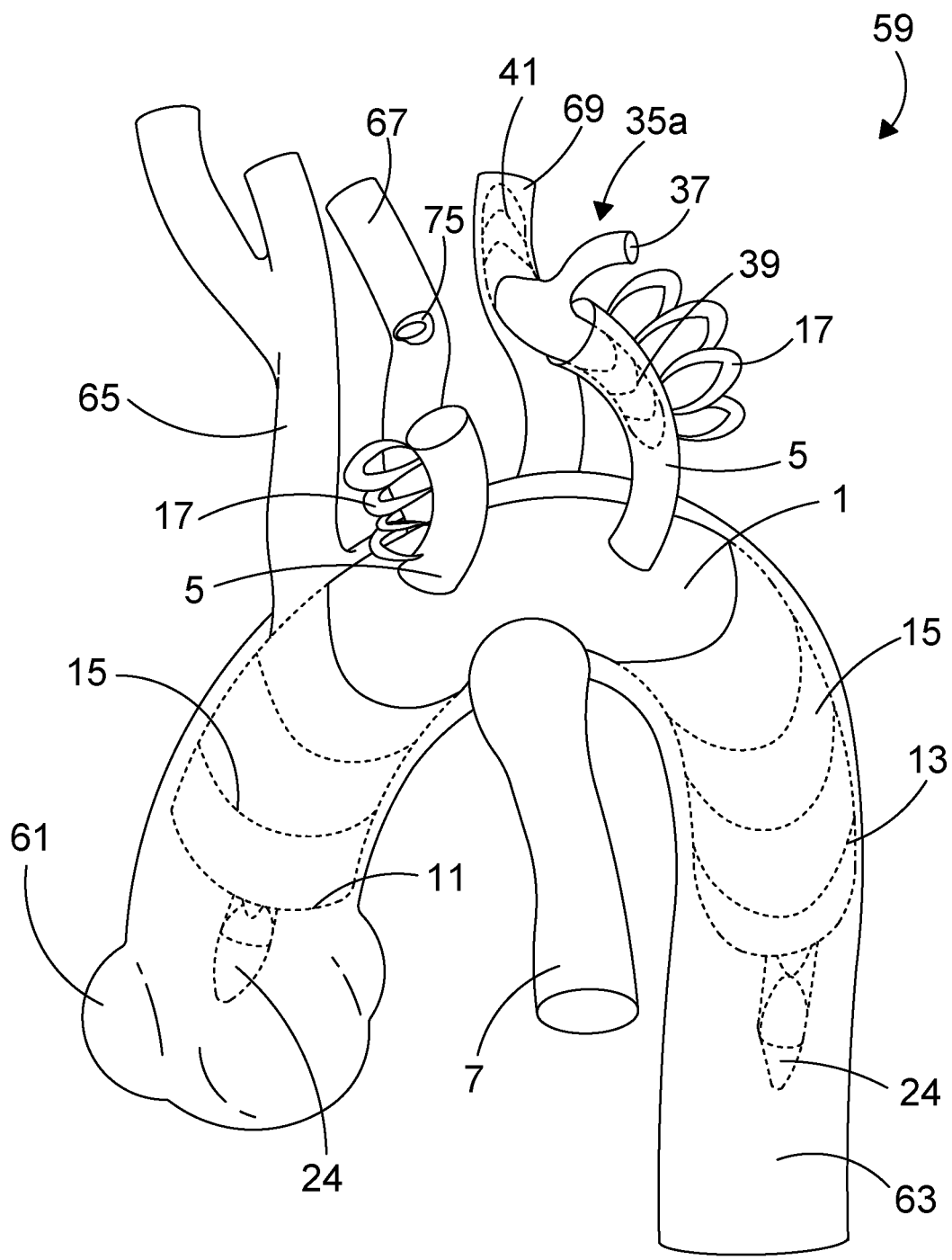
FIG. 9 illustrates the deployment of the tubular branch body into the natural (native) vessel and the docking branch of the tubular prosthetic device of FIGS. 6 and 7.

With reference to FIG. 4, (and in part to FIG. 3 for device parts), there is shown a second portion of the modular component delivery system 43. The modular component delivery system comprises a sheath 47 for confining a tubular branch body having proximal 41 and distal 39 portions in a compact form for delivery through a lumen. A press-fit retrieval pin 57 configured to fit within a separate retrieval capsule (not shown), attachable to a retrieval wire (not shown) is shown protruding from a compact (sheathed) tubular branch 55. In the depicted example, the modular component delivery system is shown to include a sheath 47 confining a compacted tubular branch body 36 (FIG. 3) of a modular component 35, and a valve 45. The example sheath 47 compacts the tubular branch proximal portion upon a delivery shaft of which a tip 49 is visible, a hub 51 including a sheath splitter and a sheath pull handle 53 for releasing the tubular branch body 36 from the sheath 47.

The sheath 47 may comprise a smooth polymeric material. A polymerised hydrofluorocarbon such as PTFE is also suitable to form the sheath 47 from. Alternatively the sheath 47 may be formed from polyethyleneterephthalate (PET). The selected material should be one which is biocompatible and may be readily passed through natural vessels or artificial lumens without sticking. The sheath 47 may be surface treated, for example to impart or enhance hydrophilic properties by applying a hydrophilic coating. Suitable polymeric flexible materials for the sheath 47 may be selected from thermoplastic polymers, elastomers, and copolymers such as nylon, polyurethane, polyethylene (PE), polytetrafluoroethylene (PTFE), expanded polytetrafluoroethylene (ePTFE), fluorinated ethylene propylene, polyether block amides (PEBA), polyimide, polyether ether ketone, and polybutylene terephthalate.

The sheath 47 may be of a multi-layered construction of flexible, polymeric materials, such as multi-layered extrusions, optionally reinforced as by use of braided layered assemblies or laminar structures incorporating bonding layers and reinforcements, or intermittent extruded composite extrusions and assemblies of variable durometer characteristics.

In an embodiment, the press-fit retrieval pin 57 may be attached to the sheath 47 whilst the retrieval capsule is attached to the retrieval wire.

In an embodiment, the press-fit retrieval pin 57 has a head portion of a shape enabling it to be captured within a corresponding recess in the retrieval capsule. The shape may be a ball, bullet or arrowhead and the head portion may be made from a resilient material allowing a degree of compression of the head portion during press-fitting into the retrieval capsule and elastic expansion of the head portion when the head portion is located in the corresponding recess in the retrieval capsule.

With reference to FIGS. 5 to 11, an example of how the endoprosthetic device 1 may be used to repair a damaged aortic arch 59 will now be described. First and second purse string sutures surrounded incisions 71, 73 are made in the aortic arch 59 in two positions to facilitate endovascular insertion of both the proximal and stented portions of the endoprosthetic device 1 into ascending 61 and descending aorta portions 63 of the aortic arch 59.

Third and fourth purse string sutures surrounding incisions 75, 77 are also made into the side walls of major vessels which typically extend from the top of the aortic arch 59 e.g. the Left Sub-Clavian Artery (LSA) 69, Left Common Carotid Artery (LCCA) 67 and Right Common Carotid Artery (RCCA)). In the depicted example, the third incision 75 is made in the LCCA 67 and the fourth incision 77 is made in the LSA 69.

The third and fourth incisions 75, 77 facilitate endovascular connections to these vessels by means of modular components 35 delivered in a similar way to the endoprosthetic device 1. These modular components 35 connect the major vessels to the device 1, to ensure that the blood supply is maintained to a cerebral region and upper limbs of a patient.

Compacted distal and proximal sections are each held inside a main tubular body sheath of the endoprosthetic device 1 are inserted through their respective purse string surrounded incisions 71, 73.

While in the compacted state the distal and proximal sections enable blood perfusion through the arch 59 to be maintained. This can be done off-pump, which requires haemostasis across the junction between the sheath and incision to be maintained and this can be controlled through tension applied across a purse string suture, both before and after the unsheathing of the distal and proximal sections.

The distal and proximal sections of the device 1 are unsheathed in rapid succession, therefore enabling blood flow to be maintained through the aortic arch. This results in the damaged aortic arch sac 59 being bi-passed through the device 1. A mid-section of the device 1 is outside of the arch 59 while the proximal and distal sections are within the damaged arch 59.

Furthermore the major branch vessels (LSA, LCCA, RCCA) at this stage are now without blood perfusion. To prevent ischemia, these are quickly re-instated and this is facilitated by the provision of modular branch components 35a, 35b.

A purse string suture and the modular component 35a are inserted through the third incision. The purse string tension is then adjusted to ensure haemostasis (to prevent blood loss between the outside of the sheath and the incision).

The other end of the modular component 35a is then inserted into the docking branch 5 of the device 1. The retrieval capsule sheath on the end of the modular component 35 is then clipped into the retrieval capsule within the device 1.

The sheath and retrieval capsule can then be withdrawn through the auxiliary branch 7. Just prior to this step it is intended to vent air and blood through the branch valve.

The sheath 82 is removed from the modular component 35a, fully deploying it so it opens up within the docking branch 7. This essentially connects the main device 1 to the native vessel, the LSA 69 in this example, so that blood supply and perfusion is therefore re-established. The intention is that this is performed quickly and efficiently to ensure that ischemia is minimised.

The docking branch 5 is provided with holding loops 17 to help locate, hold and stabilise the docking branch when connecting the modular device 35b. The docking branch 5 is also trim-able to facilitate anatomical variances without compromising their function.

Figure 10:
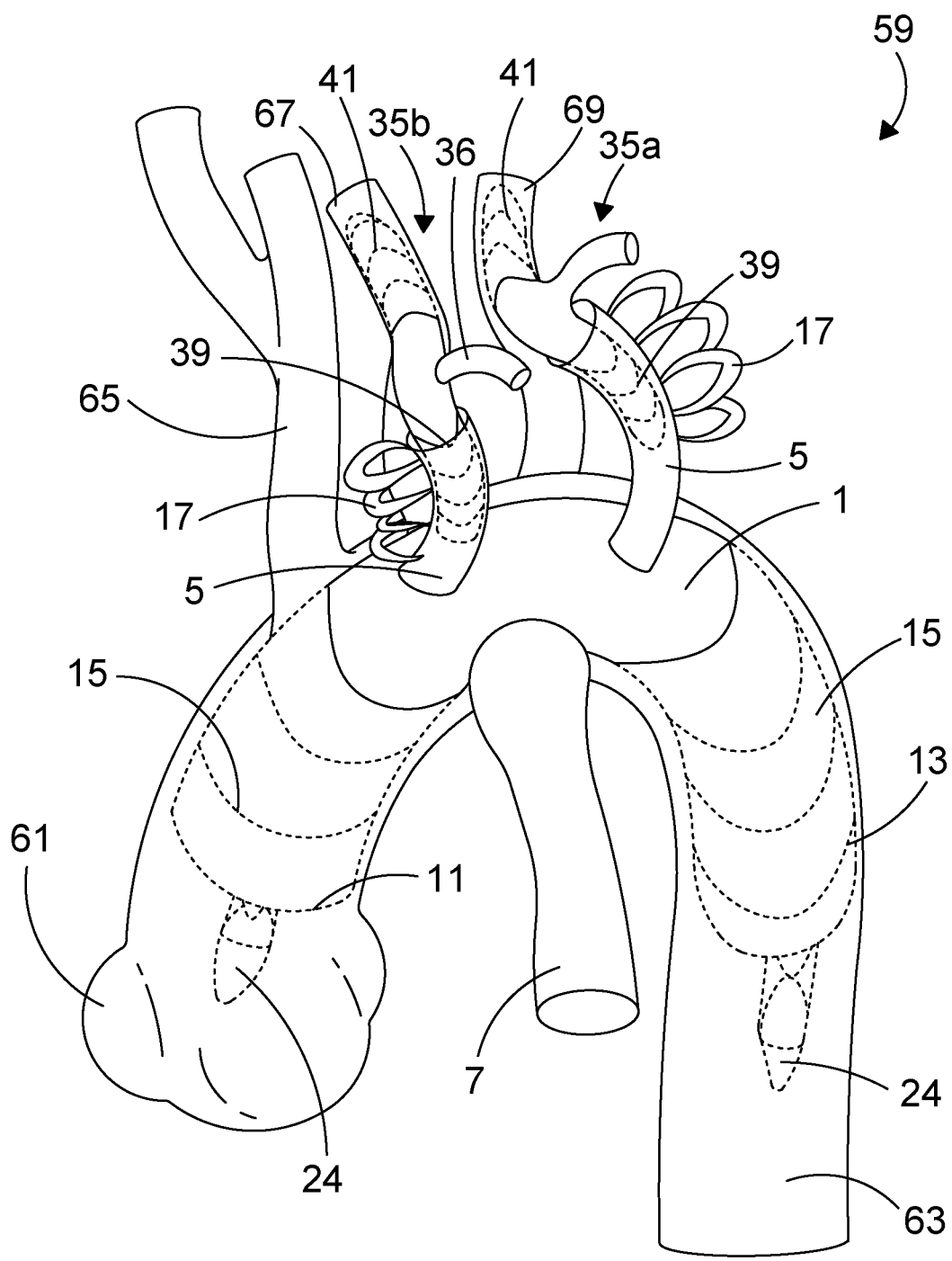
FIG. 10 illustrates the introduction and deployment of a further tubular branch body into a different docking branch of the tubular prosthetic device of FIGS. 6 and 7 to further construct the modular assembly.
Figure 11:
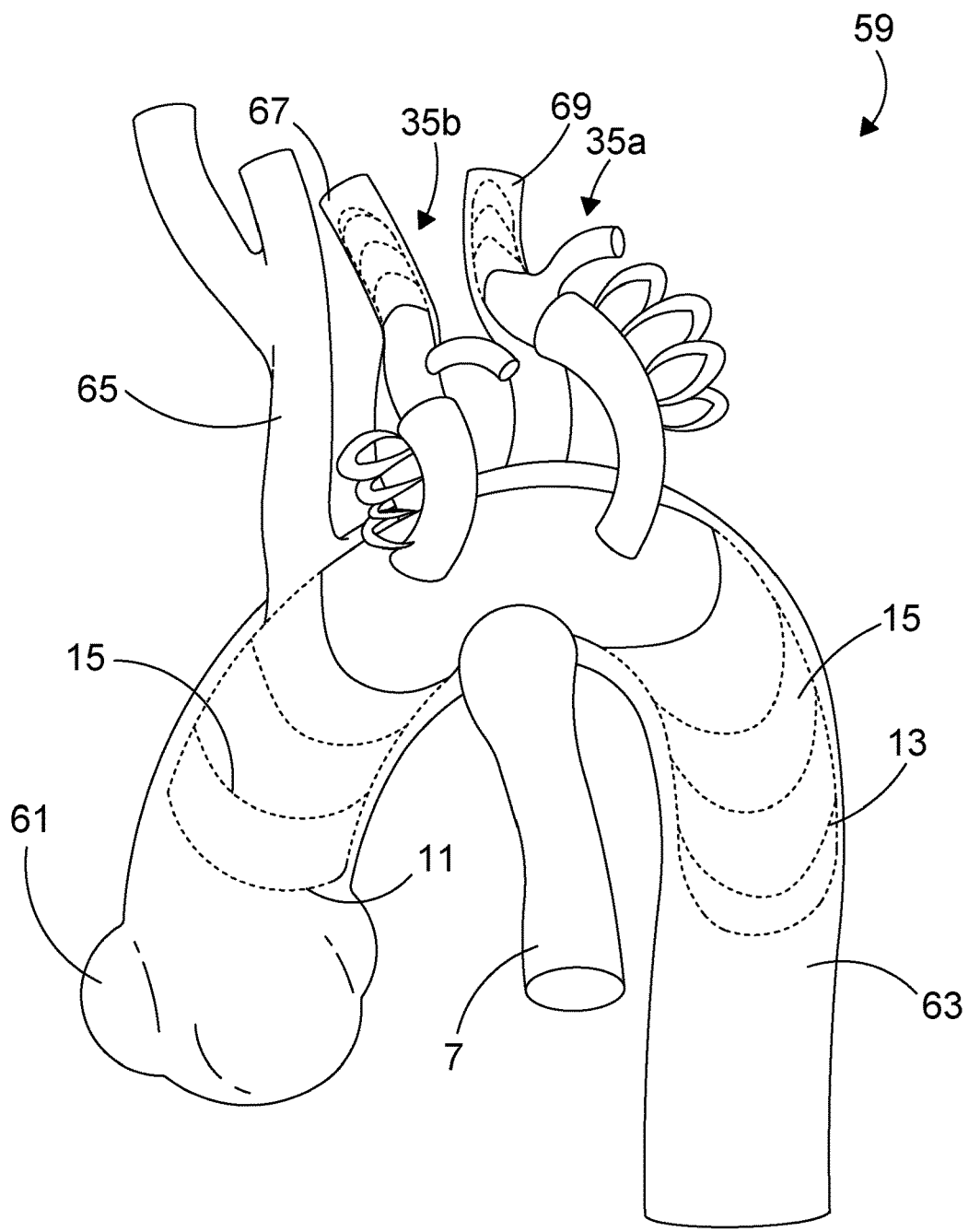
FIG. 11 illustrates the deployed modular assembly of tubular prosthetic device prior to cutting off the auxiliary branch, transection of the native aortic vessel into which the tubular prosthetic device is positioned prior to completion of the surgical procedure.
Figure 12:
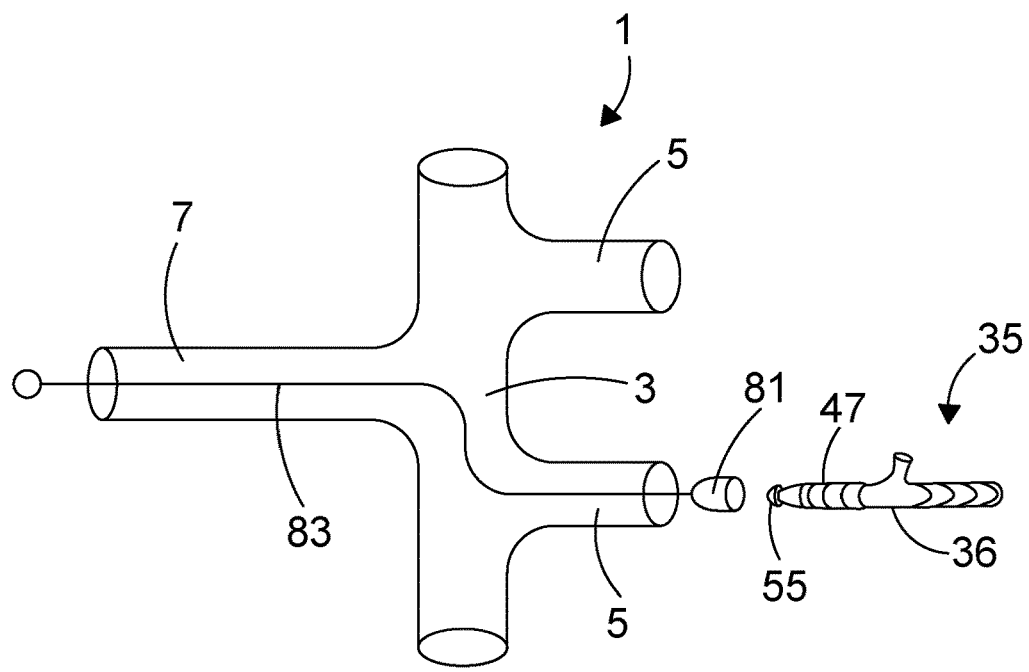
FIG. 12 schematically illustrates the main tubular body tubular of the prosthetic device having an auxiliary branch and two docking branches extending laterally, though which a retrieval wire and retrieval capsule is passed to engage with a press-fit retrieval pin associated with a tubular branch body to be assembled with the main tubular body.
Figure 13:
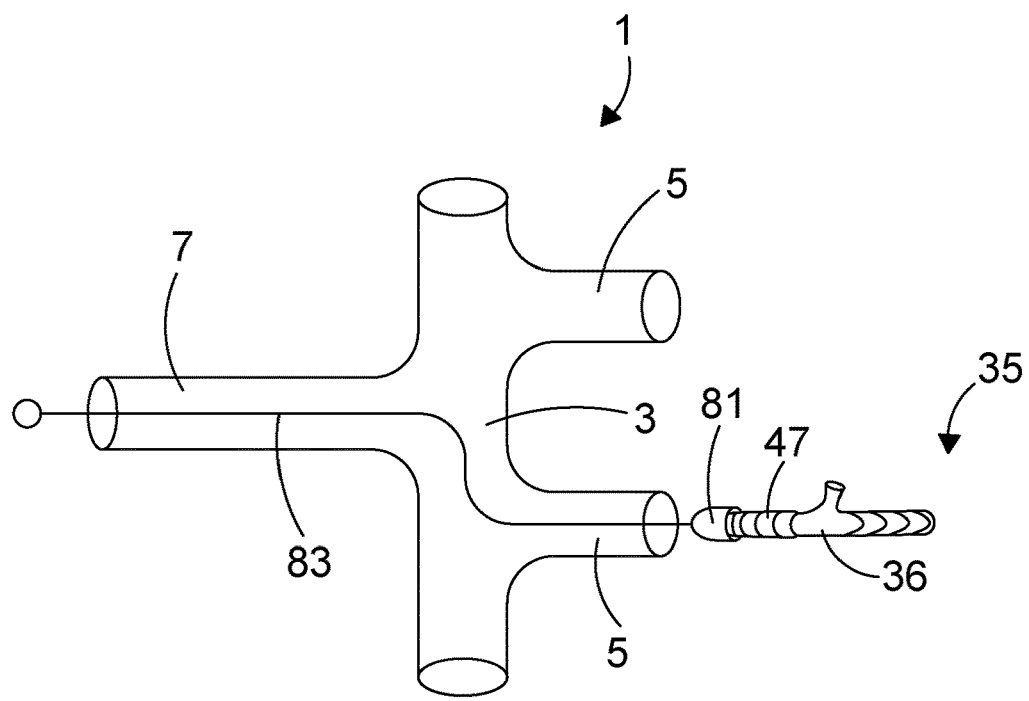
FIG. 13 schematically illustrates the connection of the retrieval capsule and retrieval pin to allow the retrieval wire to be linked with the tubular branch body.
Figure 14:
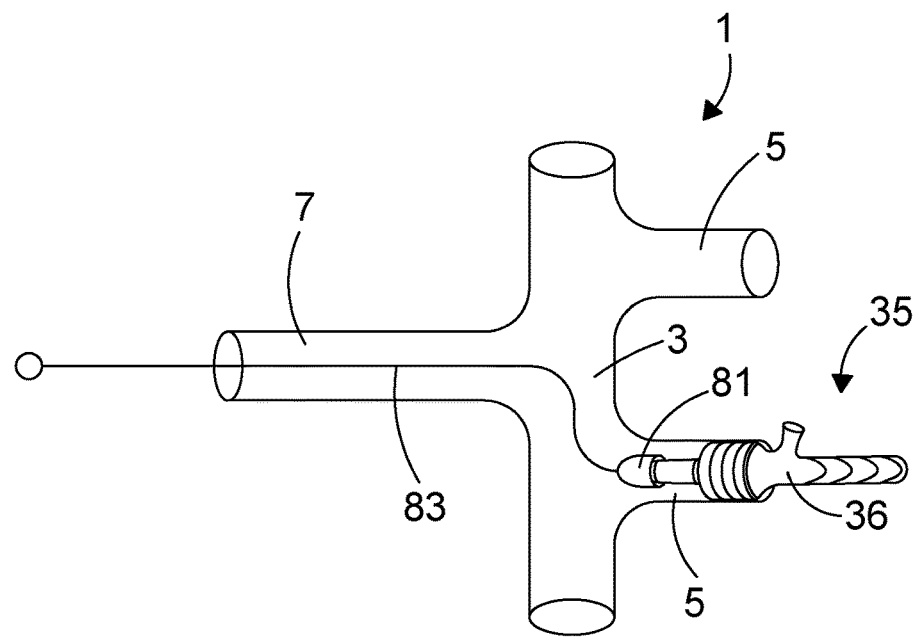
FIG. 14 schematically illustrates the introduction of the tubular branch body into the docking branch by pulling of the retrieval wire and deployment of a stented portion of the tubular branch body.
Figure 15:
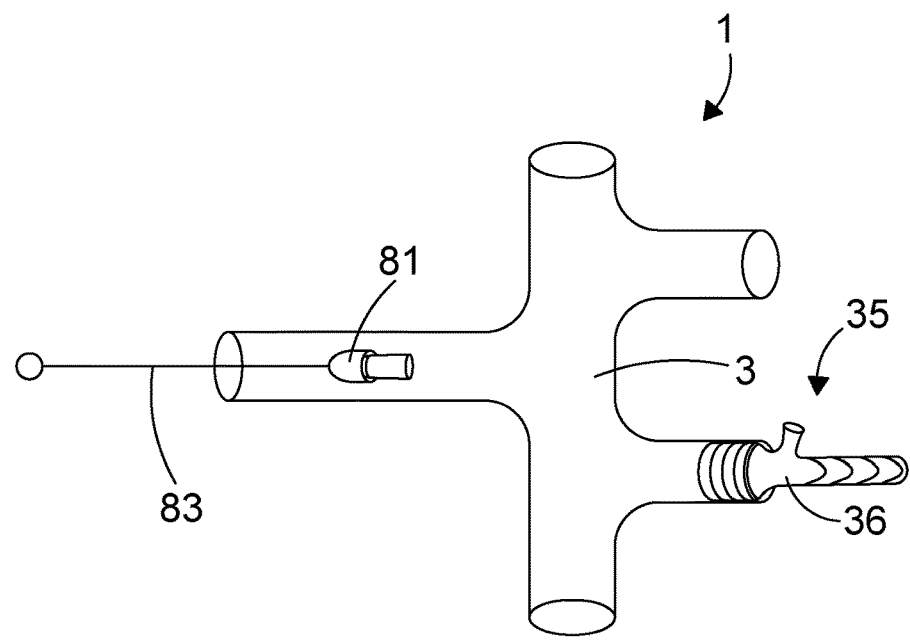
FIG. 15 schematically illustrates the withdrawal of the retrieval wire, retrieval capsule and attached retrieval pin from the deployed stented portion of a the tubular branch body.

In the depicted example, a second modular component 35b is then inserted into another docking branch 5 of the device 1 (there may be 1, 2, 3 or more docking branches, however only 2 are shown in FIGS. 10 and 11), and used connect the main device 1 to the native vessel in the same way as modular component 35a described above.

The modular branch delivery system withdraws the sheath through the auxiliary branch 7 of the device 1, which towards the end of the procedure is dissected and removed from the device 1. The auxiliary branch 7 may then be cut from the device 1.

With blood flowing through the device 1 and the LCCA and LSA, a surgeon can then transect a main trunk of the damaged aorta arch 59, with the main device placed into the cavity of the native arch vessel.

With reference to FIGS. 12 to 16, how the branch modular component delivery system 31 is used in practice will now be described. In use of such an embodiment for an endoprosthetic device 1 having a tubular main body 3 with at least one docking branch 5 extending laterally from the tubular main body 3, a user presents a tubular branch body 36 having stented portions in a compact form within a sheath 47, and having a press-fit retrieval pin 57 attached to the sheath, in juxtaposition with a retrieval capsule 81 with attached retrieval wire 83 previously passed through the tubular main body 3 via an access or auxiliary branch 5, the retrieval pin 57 is press-fitted into the retrieval capsule 81, the tubular branch body 36 is then insertable into a docking branch 5 of the main body 3 of the endoprosthetic device 1, and by pulling upon the retrieval wire 83, the tubular branch body 36 is first positioned in the docking branch of the main body of the endoprosthetic device and thereafter the stented portions of the tubular branch body is deployed by removal of the sheath 47 via the access or auxiliary branch.

The manner of removal of the sheath 47 is not limited, and for that purpose a pull strap, pull wire, or pull cord can be used to initiate removal. The sheath 47 may be designed to facilitate removal by having tearable parts, for example a lengthwise axial tear line which can be torn by contact with a pull wire to part the sheath lengthwise. Alternatively, the delivery system may incorporate a slitting tool and the sheath 47 may be designed to split (tear) in a predictable and controllable manner under application of appropriately applied force when in contact with the slitting tool.

FIGS. 12 to 16 show sequential steps of the connection of the modular branch component 35 to the main body component 3 and the same reference numerals are used to identify the same parts as used above throughout the sequence.

Figure 16:
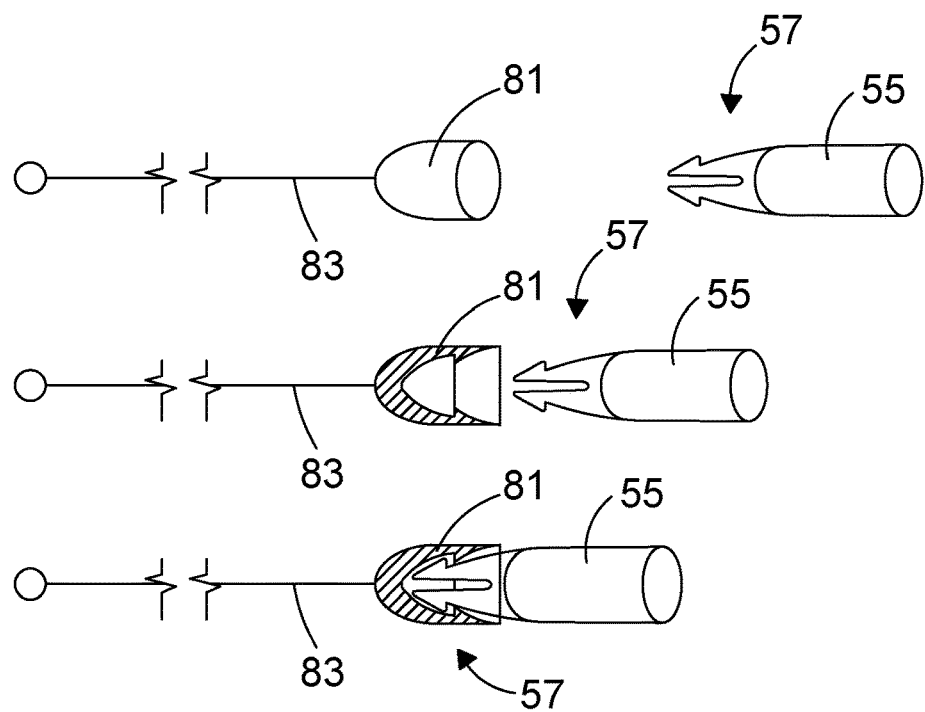
FIG. 16 schematically illustrates in three sequential stages the connection of a retrieval capsule and a press-fit split arrowhead pin.

With reference to FIG. 16, there is shown in detail three sequential stages of the connection of a retrieval capsule 81 and the retrieval pin 57. In the depicted example, the shape of the head portion of the retrieval pin 57 is shown to be that of an arrowhead. In the first stage of the connection process, the head portion is aligned with the retrieval capsule 81. In the second stage of the process, the head portion is press-fitted within the retrieval capsule 81. When the head portion is press-fitted inside the retrieval capsule 81 it undergoes a degree of compression to allow it to enter the retrieval capsule 81 and then undergoes a degree of elastic expansion to retain it inside the retrieval capsule 81.

Figure 17:
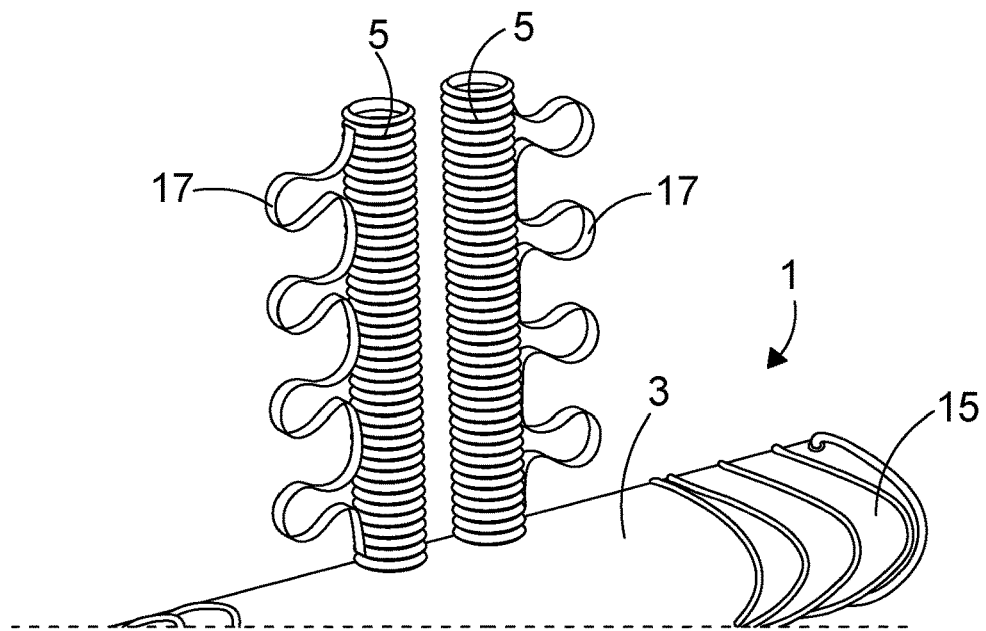
FIG. 17 illustrates adjustable length docking branches having a series of holding loops extending outwardly from the crimped surface of each docking branch.

With reference to FIG. 17, there is shown as an example adjustable length docking branches 5 for the endoprosthetic device 1. Each adjustable length docking branch is shown to extend laterally from the tubular main body 3, and to comprise a crimped fabric sleeve enabling the docking branch 5 to be stretched along its length and when required curved in a desired direction. In the depicted example, the adjustable length docking branch 5 has a length comprising a series of sections and each section is provided with a holding loop 17.

Figure 18:
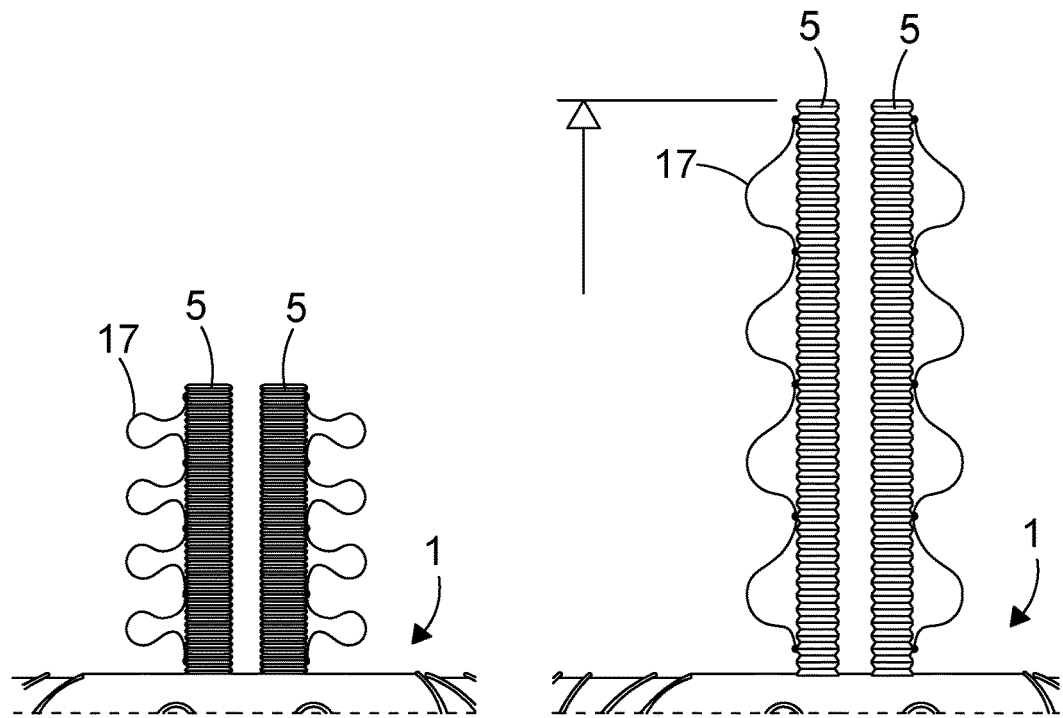
FIG. 18 illustrates in sequential side by side views the lengthwise stretch capability of the looped docking branches.

FIG. 18 shows the capability of the docking branch 5 to adjust in length when a stretch is applied to the docking branch 5.

Figure 19:
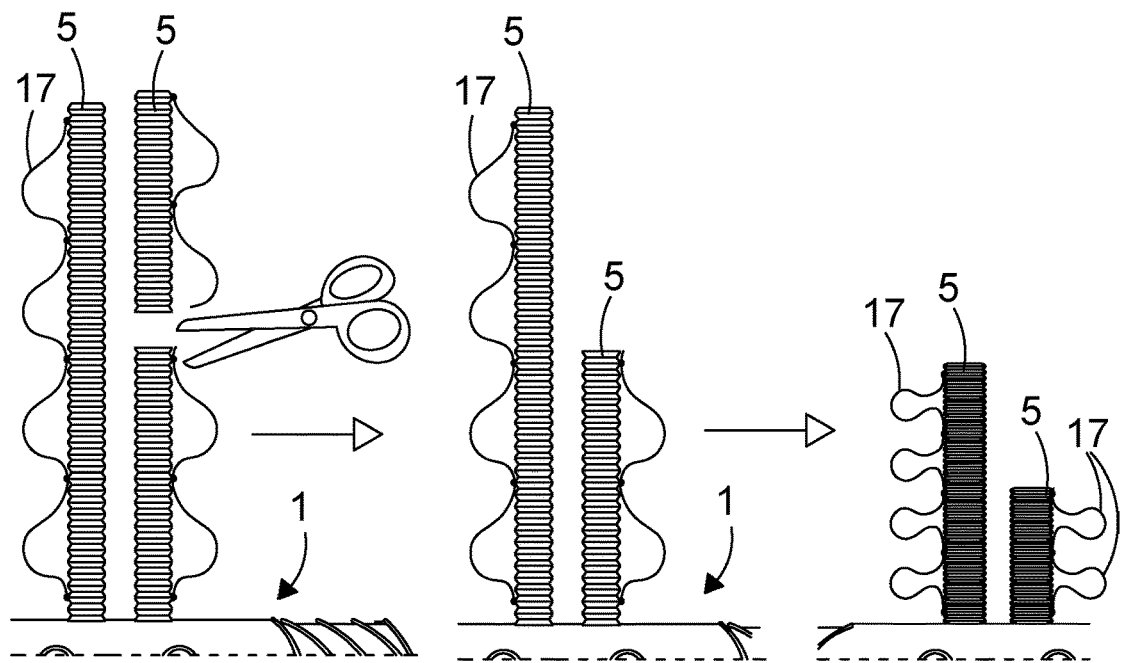
FIG. 19 illustrates in sequential series a sizing step where the looped docking branches are initially stretched, one docking branch is shortened by cutting off a selected length portion, and the looped docking branches are returned to an unstretched configuration.
Figure 20:
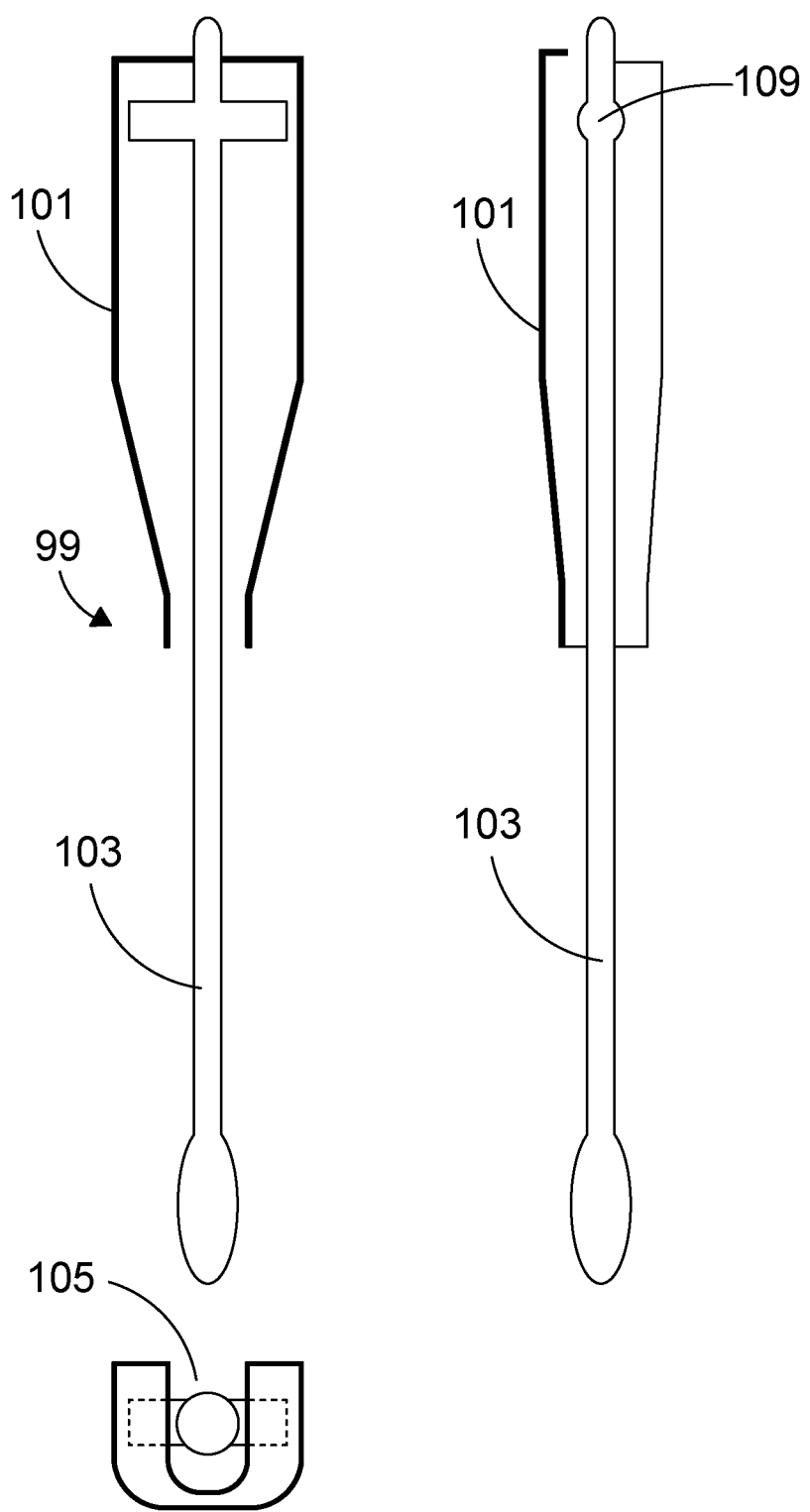
FIG. 20 shows in respective upper and lower figures, a view from one side of a delivery shaft bearing a pivotal housing (shown in cross-section) with an end elevation, and a plan view of a delivery shaft bearing a pivotal housing (shown in part-section), in both figures omitting a device for clarity.
Figure 21:
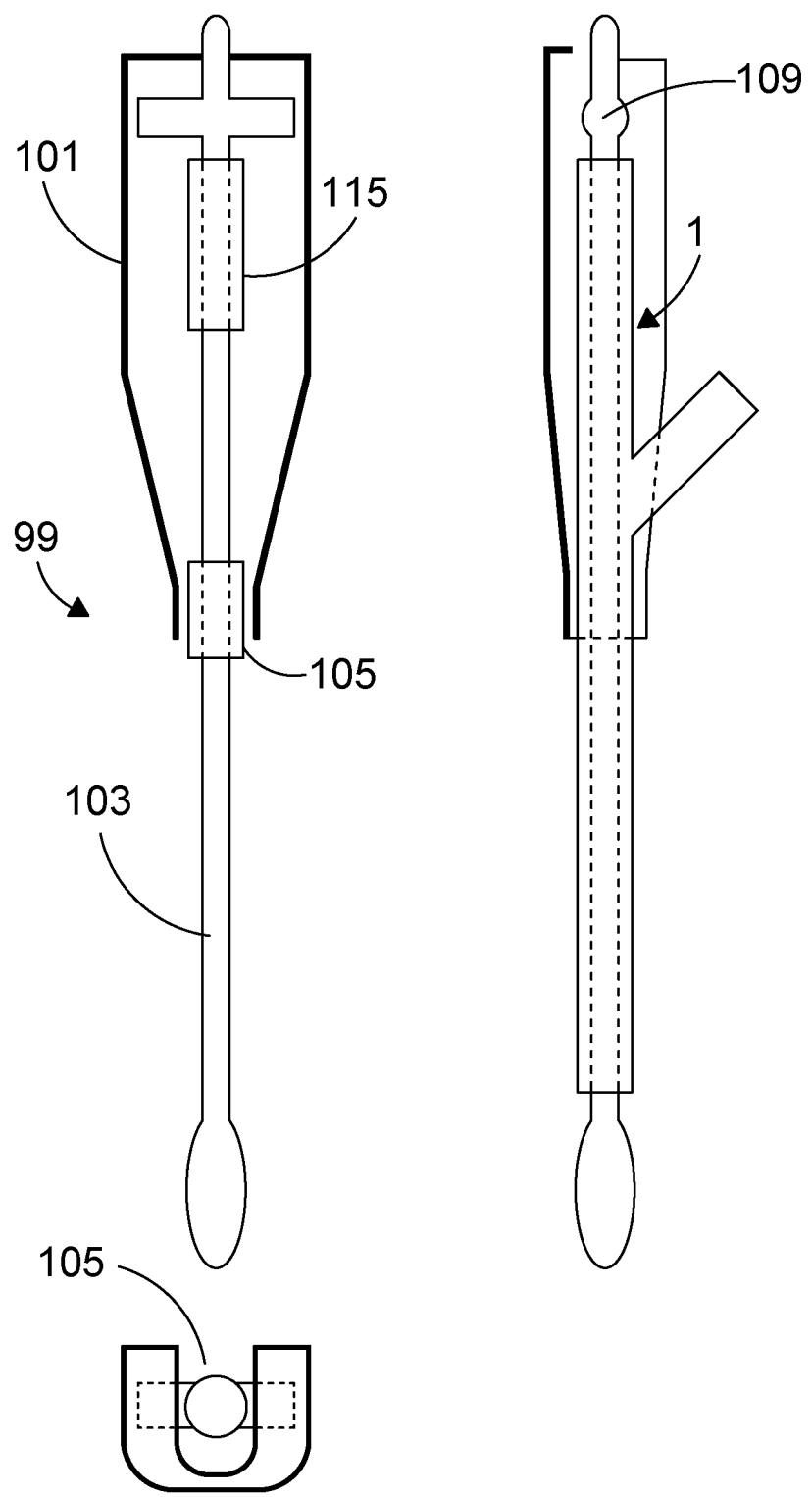
FIG. 21 shows in respective upper and lower figures, the delivery shaft and housing of FIG. 20 and additionally showing in the upper figure positioning of a first pivotal C-clamp grip valve and a second integral valve and vent which may remain resident in an access/auxiliary branch after withdrawal of the delivery shaft; and in the lower figure a tubular branch device with one limb thereof and an access branch upon the delivery shaft represented by a fabric sleeve and another limb of the tubular branch device extending to one side.
Figure 22:
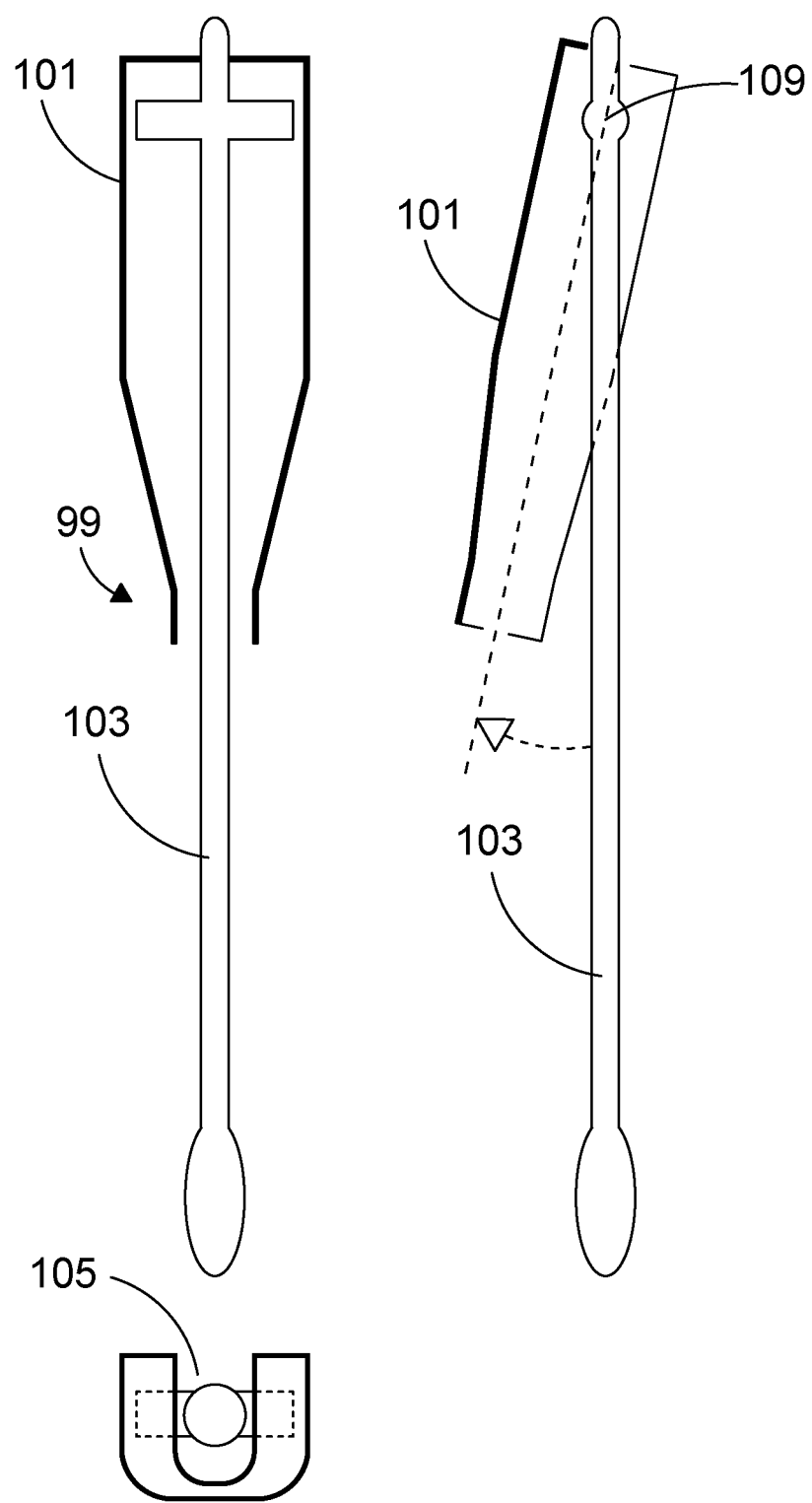
FIG. 22 shows in respective upper and lower figures the in-line and pivoted positions of the housing upon the delivery shaft, again omitting a device for illustration purposes.
Figure 23:
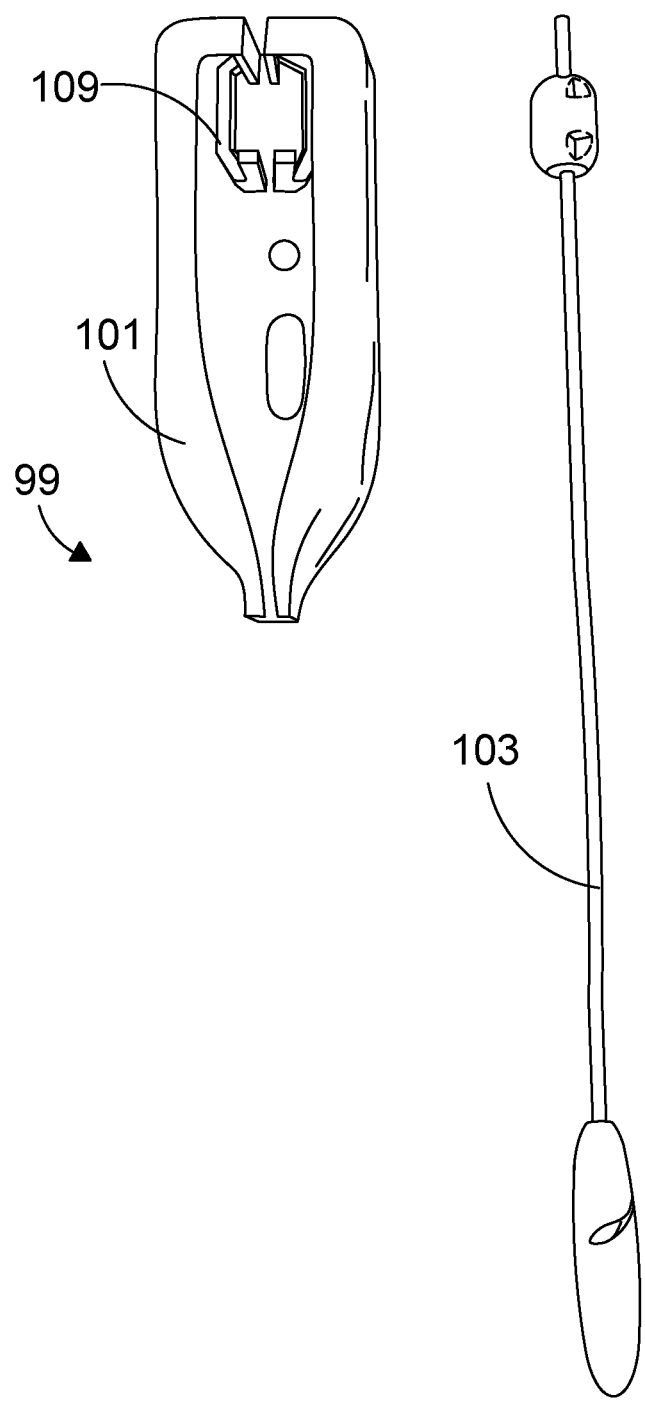
FIG. 23 shows an embodiment of a C-clamp grip valve housing separated from a delivery shaft to reveal the location of the pivotal mounting hub distally positioned with respect to the integral tip of the delivery shaft.
Figure 24:
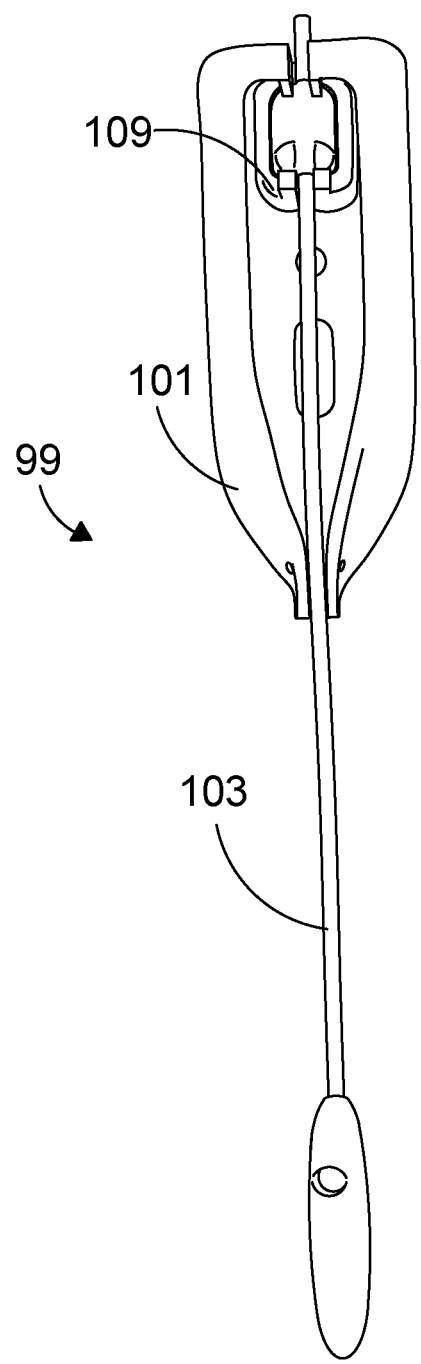
FIG. 24 shows the embodiment of FIG. 23 assembled and viewed from one side.
Figure 25:
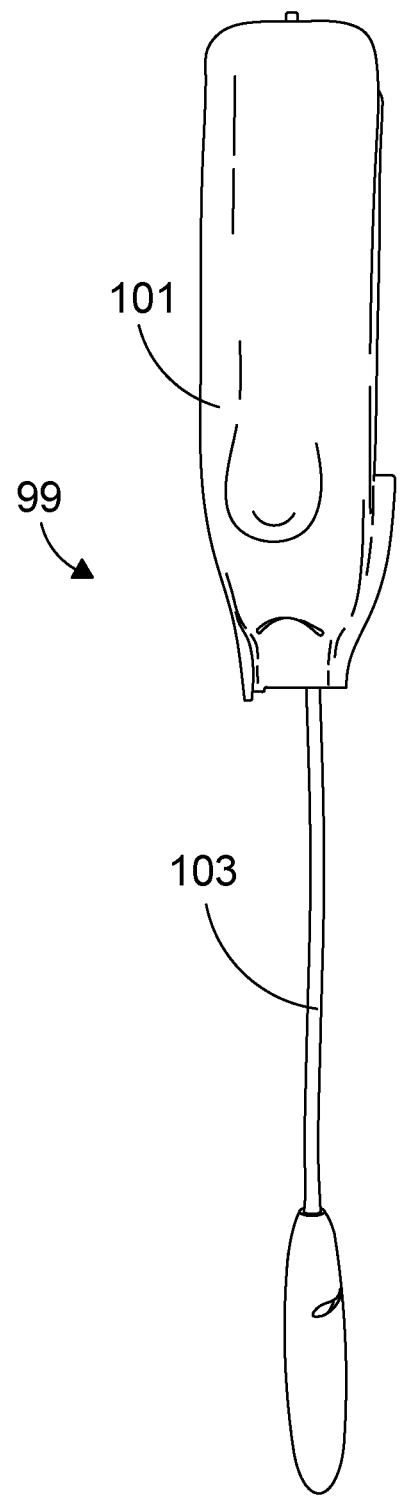
FIG. 25 shows the embodiment of FIGS. 23 and 24 assembled and from above.
Figure 26:
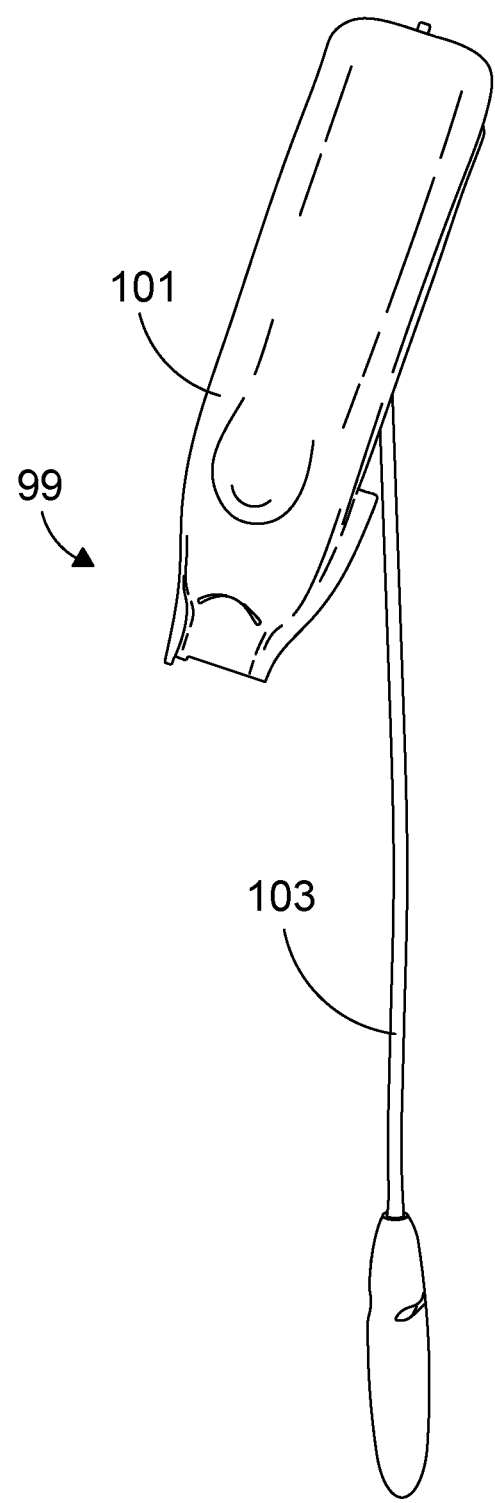
FIG. 26 shows the same embodiment of FIGS. 23-25 with the pivotal housing in a pivoted position to remove the C-clamp grip valve from about the delivery shaft.
Figure 27:
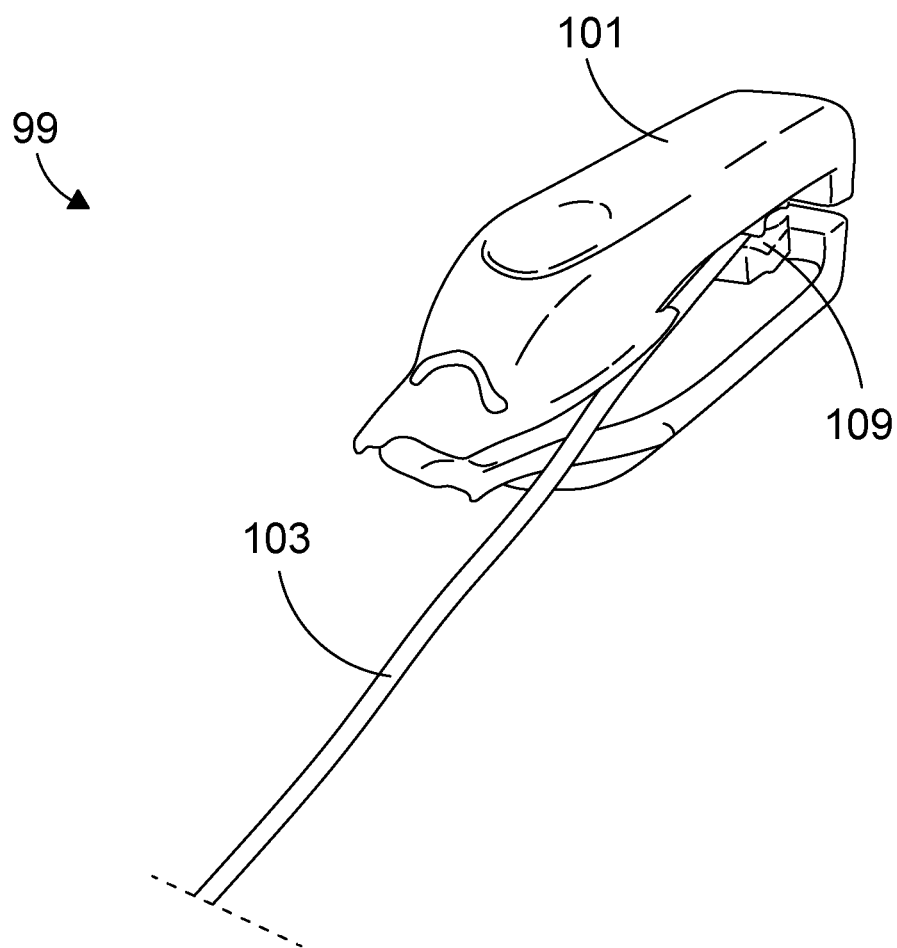
FIG. 27 shows the same embodiment of FIG. 26 from the side and from the distal end of the delivery shaft to show the configuration of the C-clamp type valve.
Figure 28:
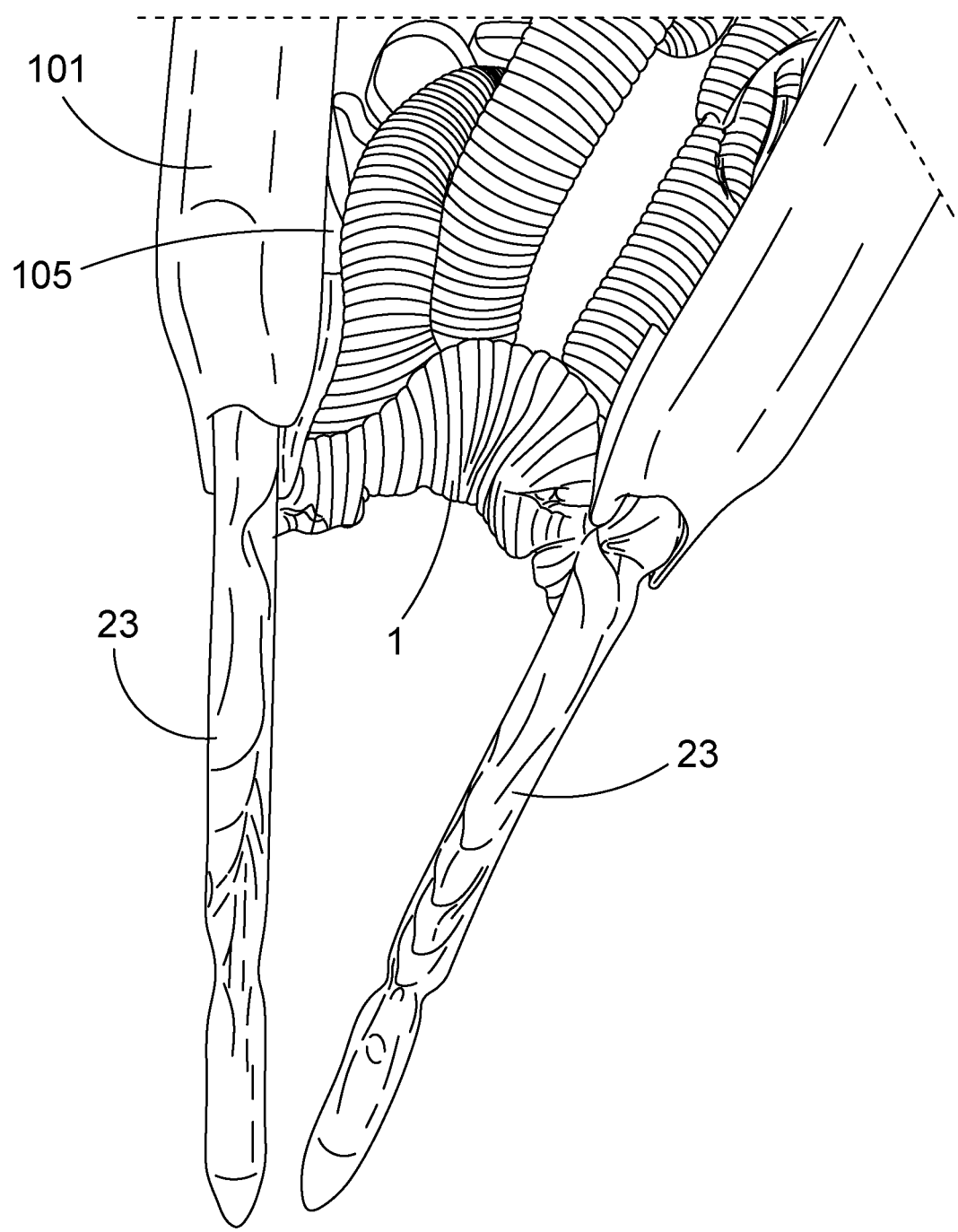
FIG. 28 shows a delivery system with sheathed devices upon delivery shafts.
Figure 29:
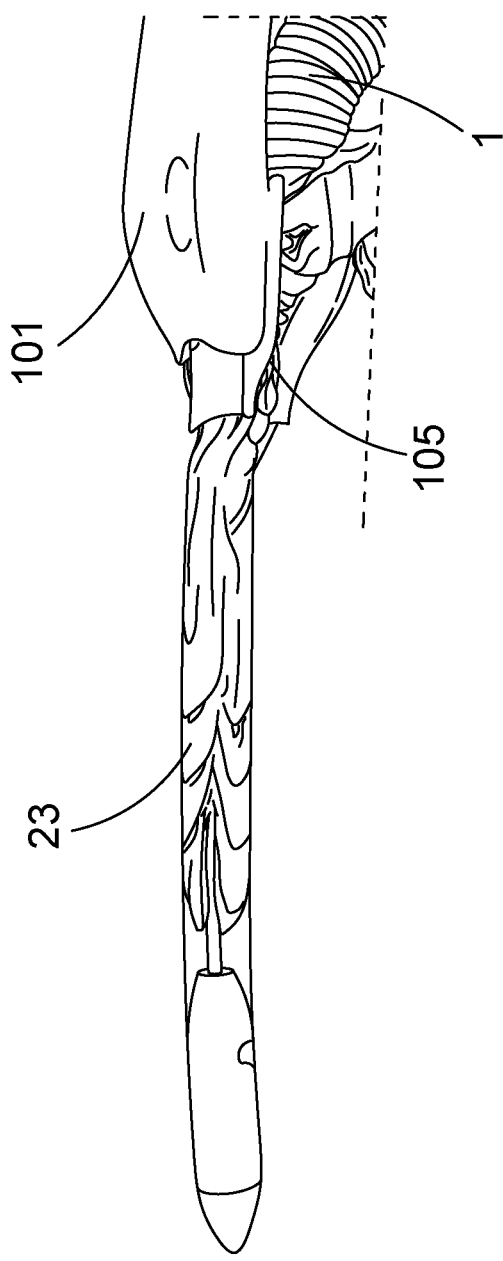
FIG. 29 shows the delivery system of FIG. 28 from one side showing a sheathed device before release.
Figure 30:
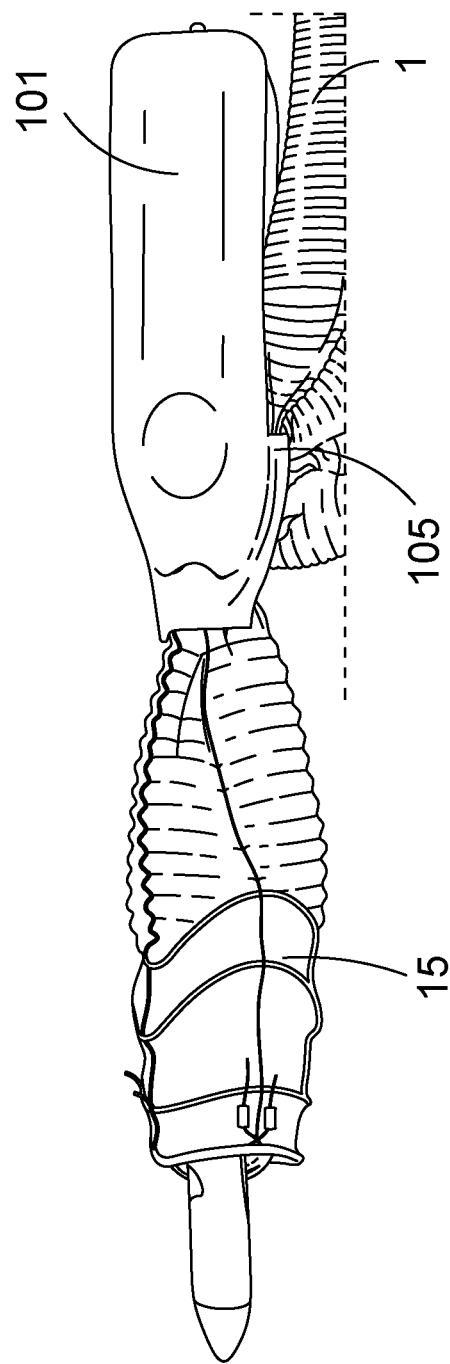
FIG. 30 shows the delivery system of FIG. 28 from one side showing an unsheathed device before removal of the delivery shaft.
Figure 31:
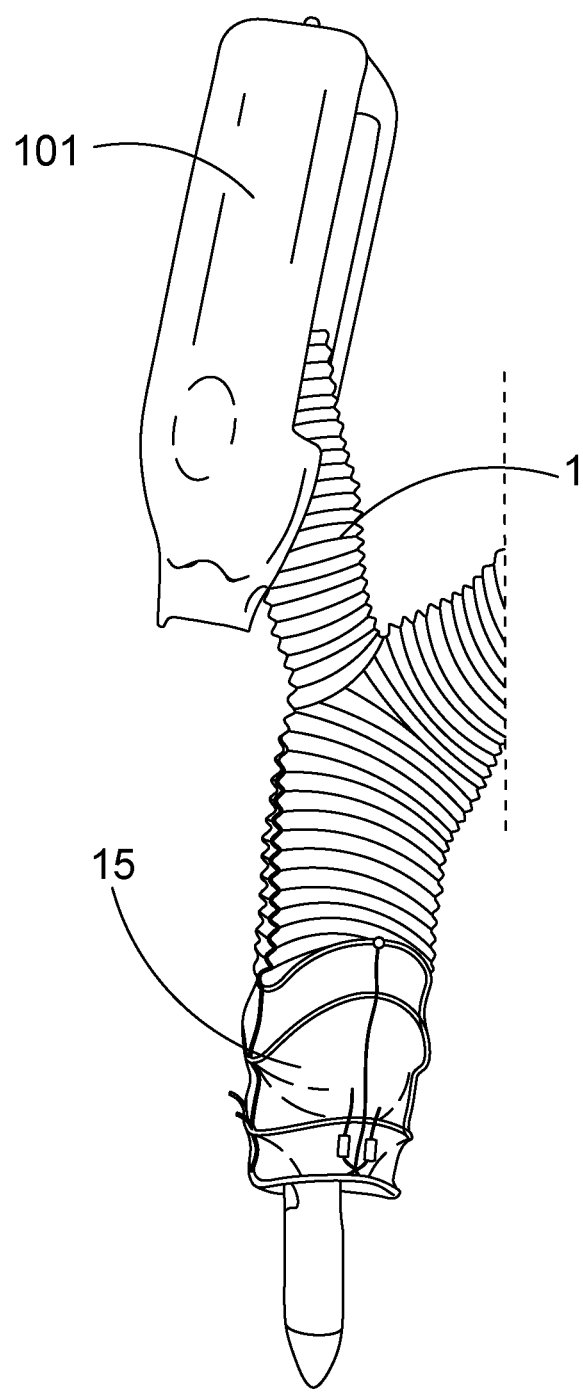
FIG. 31 shows the C-clamp valve housing pivoted away from the delivery shaft to release device fabric from the "C" grip of the C-clamp valve, to permit removal of all parts of the delivery system from the device.
Figure 32:
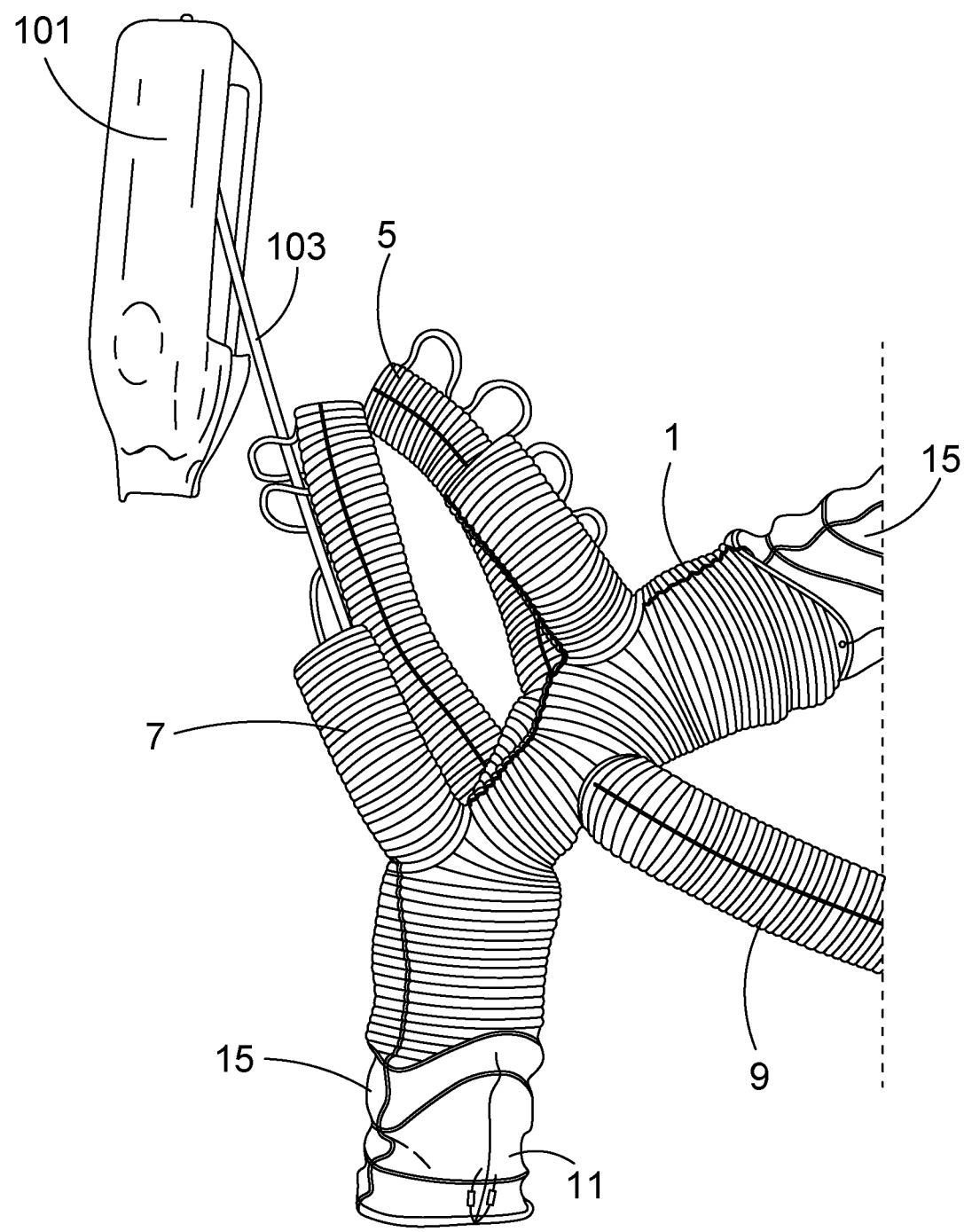
FIG. 32 shows partial removal of the delivery shaft and housing from the open (deployed configuration) device.
Figure 33:
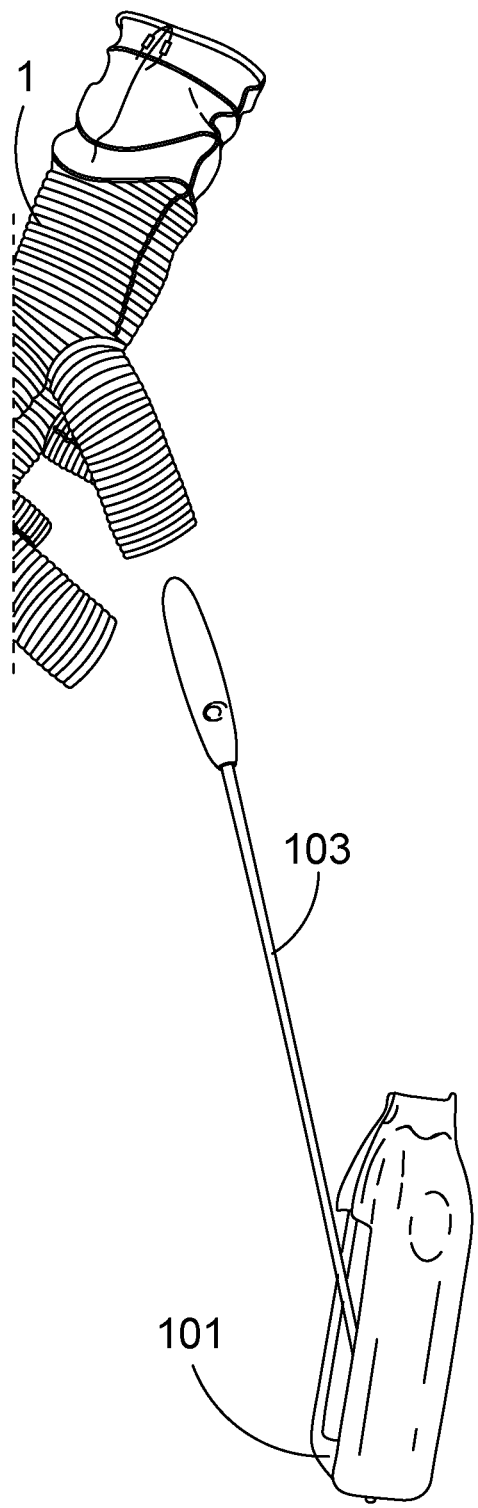
FIG. 33 shows complete removal of the delivery shaft and housing from the open (deployed configuration) device.

As shown in FIG. 19, in use, the surgeon may initially stretch the docking branch 5 so that it increases in length and then shorten the branch 5 to the desired length by cutting the branch 5 with a cutting tool. The docking branches 5 then return to an unstretched configuration.

With reference to FIGS. 20 to 33, a valve and air venting capability 99 is introduced into an auxiliary or access branch 7 of the main tubular body 3 by provision of at least a removable valve 113 and an integral valve/vent 115 deliverable upon a delivery shaft 103. The valve and air venting capability 99 may comprise a slotted housing 101 configured around a delivery shaft 103 upon which a device 1 may be mounted and constrained in a compact form within a removable sheath 23, the slotted housing 101 forming a removable C-shape clamp valve part 105 about the delivery shaft 103 and compact endoprosthetic device 1 positioned upon the delivery shaft 103. The housing may be pivotally mounted upon the delivery shaft 103 to allow the C-shape clamp valve part 105 to be removed from gripping about the delivery shaft 103 and endoprosthetic device 1 during or after deployment of the endoprosthetic device 1 by removal of the sheath 23. The pivotal mounting 109 for the housing 101 may be located and spaced distally on the delivery shaft 103 with respect to the position of the C-shape valve part 105. The housing 101 may include a chamber for enclosing the integral valve and vent positioned upon the delivery shaft 103, which integral valve/vent 115 may be resident within the access branch of the device 1 after removal of the delivery shaft 103, and removed subsequently in the procedure when the access branch is to be cut down and sutured closed, the integral valve 115 and vent being removable with the cut off access branch fabric to be disposed of.

The housing 101 may be configured to serve as a user handle for manipulation and control of the delivery system 21.

NUMERALS USED IN THE DRAWINGS (FOR REFERENCE ONLY)

Endoprosthetic device 1
Tubular main body 3
Docking branch 5
Auxiliary Branch 7
Main body access branches 9
Proximal Stented Portion 11
Distal Stented Portion 13
Stent 15
Holding loops 17
Delivery system 21
Main tubular body sheaths 23
Delivery System Tip 24
Splitters 25
Handles 27
Capsule support holder 29
First portion of modular branch delivery system 31
First Valve 33
Modular branch 35
First Modular Branch 35a
Second Modular Branch 35b
Tubular branch body 36
Access Branch 37
Distal stented section 39
Proximal stented section 41
Second Portion of the modular branch delivery system 43
Second Valve 45
Modular Graft Sheath 47
Tip 49
Sheath splitter 51
Handle 53
Compact (sheathed) tubular branch 55
Press Fit Retrieval Pin 57
Aortic Arch 59
Ascending Aorta 61
Descending Aorta 63
Brachiocephalic Artery 65
Left Common Carotid Artery 67
Left Subclavian Artery 69
First Incision 71
Second Incision 73
Third Incision 75
Fourth Incision 77
Retrieval Capsule 81
Retrieval wire 83
Venting system 99
Slotted Housing 101
Delivery Shaft 103
C-shape clamp valve part 105
Transverse member 107
Pivotal mounting 109
Removable valve 113
Integral valve 115

The invention claimed is:

1. A delivery system comprising:
a) a sheath;
b) a retrieval capsule;
c) a press-fit retrieval pin that is press-fit within the retrieval capsule;
d) a retrieval wire having a proximal end and a distal end, wherein one of the retrieval capsule and the press-fit retrieval pin is attached to the sheath, and the other one of the retrieval capsule and the press-fit retrieval pin is attached to the distal end of the retrieval wire, the proximal end of the retrieval wire being available to a user of the system, wherein pulling the retrieval wire by the user causes movement of the sheath;
e) at least one tubular branch body, the at least one tubular branch body including a proximal stented portion and a distal stented portion, a tubular branch body flexible portion linking the proximal stented portion and the distal stented portion, and a tubular branch body access branch extending laterally from the tubular branch body flexible portion, and wherein the sheath confines at least a portion of the at least one tubular branch body and is removable from the at least one tubular branch body by pulling the retrieval wire; and
f) an endoprosthetic device, the endoprosthetic device including a tubular main body having a proximal portion, a distal portion and a flexible portion linking the proximal portion and the distal portion, the endoprosthetic device further including at least one docking branch of adjustable length extending laterally from the tubular main body, wherein the at least one docking branch of the endoprosthetic device is mateable with the proximal stented portion of the tubular branch body to thereby form a vascular graft modular assembly, and at least one tubular body access branch extending laterally from the tubular main body.

2. The delivery system of claim 1, wherein at least one of the proximal portion and the distal portion of the tubular main body includes a stent.

3. The delivery system of claim 1, wherein the proximal portion and the distal portion of the tubular main body each include a stent.

4. The delivery system of claim 1, wherein at least a portion of the at least one docking branch includes a crimped fabric.

5. The delivery system of claim 4, wherein the crimped fabric includes expanded polytetrafluoroethylene (ePTFE) or polyester.

6. The delivery system of claim 1, wherein the at least one adjustable length docking branch has a length that includes a series of sections, each section having a tab that can be gripped by the user.

7. The delivery system of claim 1, wherein the at least one adjustable length docking branch has a length that includes a series of sections, each section having a loop that can be gripped by the user.

8. The delivery system of claim 7, wherein the loop is made of a biocompatible material.

9. The delivery system of claim 1, wherein the endoprosthesis device further includes at least one auxiliary branch extending from the tubular main body.

10. The delivery system of claim 9, wherein the endoprosthetic device further includes an integrated valve.

11. The delivery system of claim 1, wherein the at least one tubular branch body is a plurality of tubular branch bodies, the at least one docking branch of the endoprosthetic device is a plurality of docking branches, and wherein the plurality of tubular branch bodies are mateable with the plurality of docking branches of the endoprosthetic device.

12. The delivery system of claim 11, wherein the endoprosthetic device includes at least four of the docking branches and the vascular graft modular assembly includes at least four of the tubular branch bodies.

13. The delivery system of claim 1, wherein the press-fit retrieval pin is attached to the sheath and the retrieval capsule is attached to the retrieval wire.

14. The delivery system of claim 1, wherein the press-fit retrieval pin includes a head portion having a shape of a ball, a bullet or an arrowhead, and includes a resilient material, wherein the press-fit includes compression of the head portion and elastic expansion of the retrieval capsule when the head portion is located in the corresponding recess of the retrieval capsule.

* * * * *